United States Patent [19]

Mueller et al.

[11] 4,221,974
[45] Sep. 9, 1980

[54] LUMBER INSPECTION AND OPTIMIZATION SYSTEM

[75] Inventors: Paul A. Mueller, Detroit; John R. Hartz, Southfield; Elaine D. Pawlowski, Wixom; M. David Freedman, Southfield, all of Mich.

[73] Assignee: The Bendix Corporation, Southfield, Mich.

[21] Appl. No.: 8,891

[22] Filed: Feb. 2, 1979

Related U.S. Application Data

[60] Continuation-in-part of Ser. No. 933,393, Aug. 14, 1978, which is a division of Ser. No. 818,252, Jul. 22, 1977, Pat. No. 4,149,089, which is a continuation of Ser. No. 638,116, Dec. 5, 1975, abandoned.

[51] Int. Cl.² .......................................... G01N 21/32
[52] U.S. Cl. .................................. 250/563; 364/475
[58] Field of Search ............... 250/560, 562, 563, 571, 250/572; 144/312; 364/468, 470, 475, 560, 561, 562, 563

[56] References Cited

U.S. PATENT DOCUMENTS

| | | | |
|---|---|---|---|
| 3,983,403 | 9/1976 | Dahlstrom et al. | 250/560 |
| 4,152,767 | 5/1979 | Laliotis | 364/560 |
| 4,164,248 | 8/1979 | Rysti | 144/312 |

*Primary Examiner*—David C. Nelms
*Attorney, Agent, or Firm*—James R. Ignatowski

[57] ABSTRACT

A lumber inspection and optimization system is disclosed combining the speed of electro-optic scanning for flaw detection with electronic data manipulation and computation for optimizing the utilization of the lumber in accordance with an order entry list specifying the dimensions, grade and priority of products desired to be cut from each board inspected by the system. The system receives input data from an order entry device and an electro-optical scanner. Digital scan data from the electro-optical scanner is electronically processed to form a flaw data buffer containing the edge location of all the detected flaws enlarged to compensate for defective material usually surrounding each flaw. Optimization of the material is accomplished by electronically comparing the order entry data with the location of the flaws in the flaw buffer to generate cut line data indicative of where the board is to be cut. The cut line data may be used to either actuate a saw to cut the lumber at the locations specified by the cut line data or actuate a marker to mark the lumber at the specified locations. When the order entry list includes products having permitted defects, the disclosed system includes a defect classification input device permitting a human inspector to insert defect classification data into the flaw data buffer prior to optimization. The preferred embodiment utilizes a mini computer programmed to process the flaw data, optimize the utilization of the board inspected and generate the cut line data.

37 Claims, 44 Drawing Figures

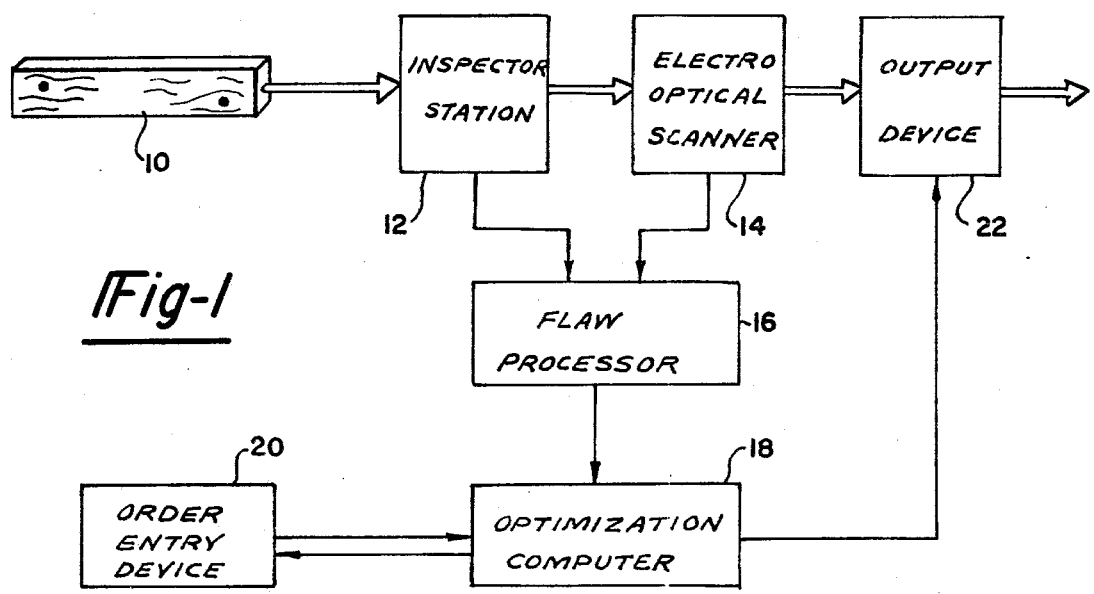
*Fig-1*
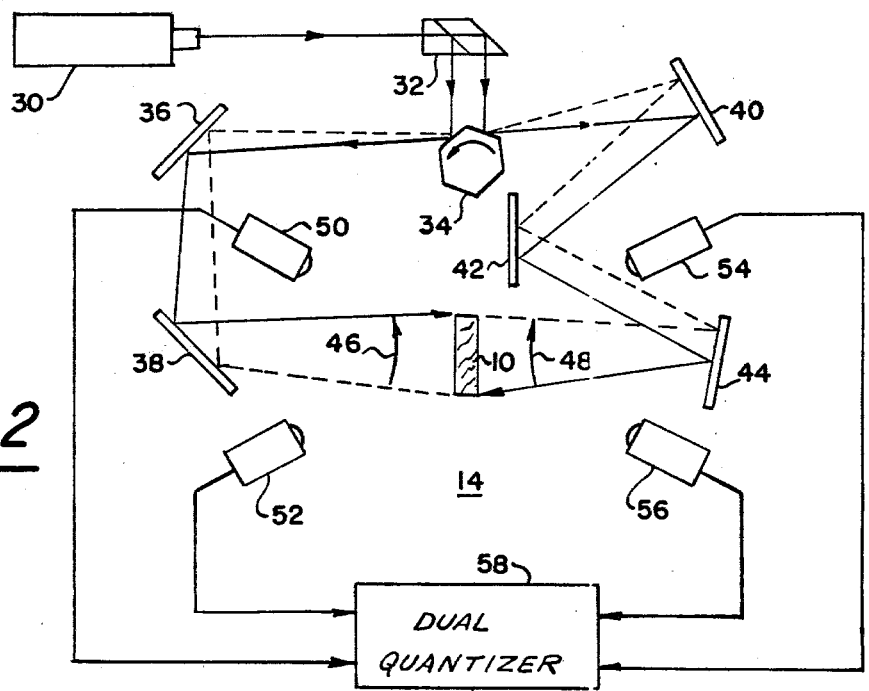
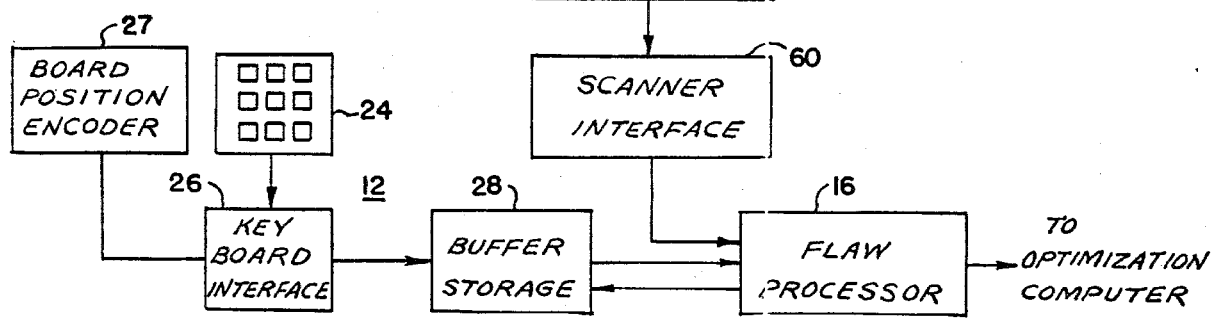
*Fig-2*

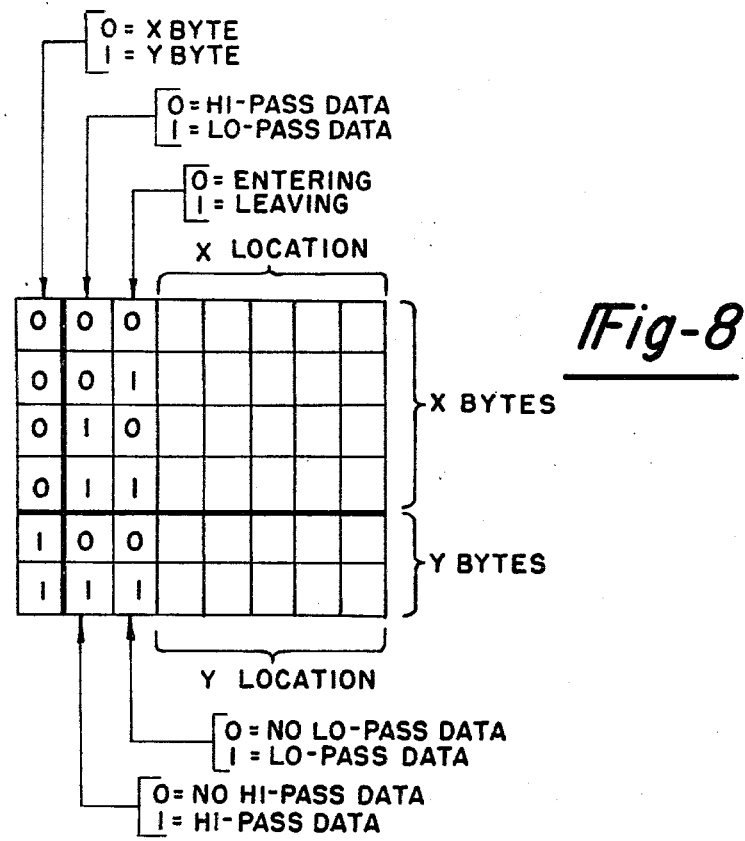
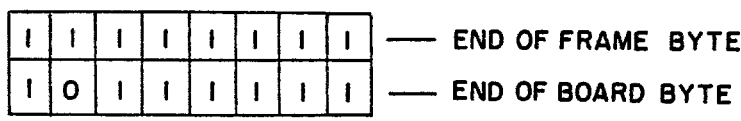
SPECIAL END OF FRAME AND END OF BOARD FORMATS
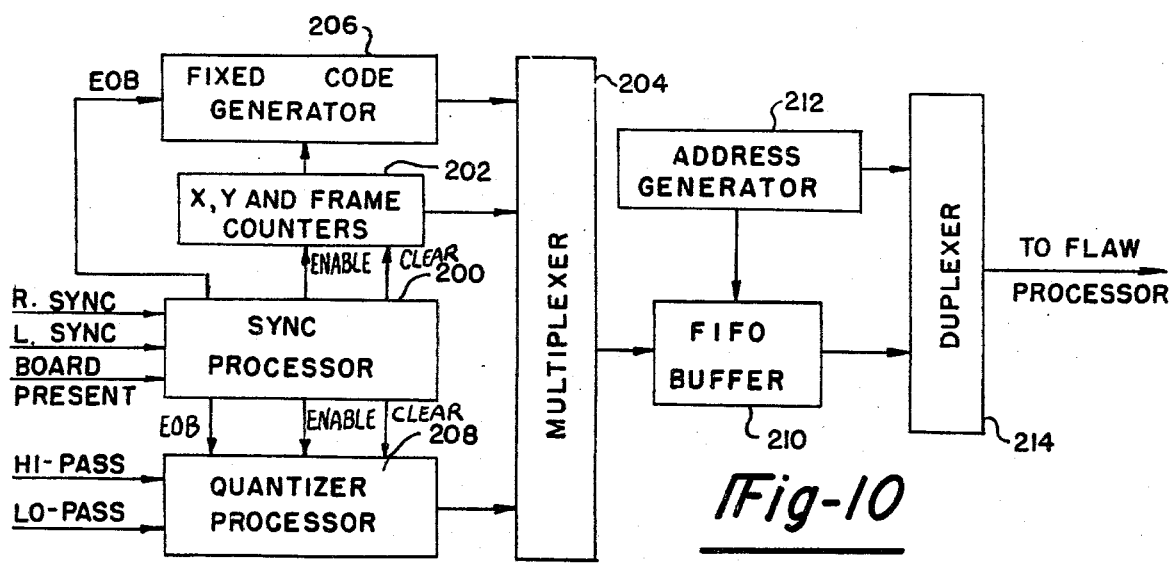

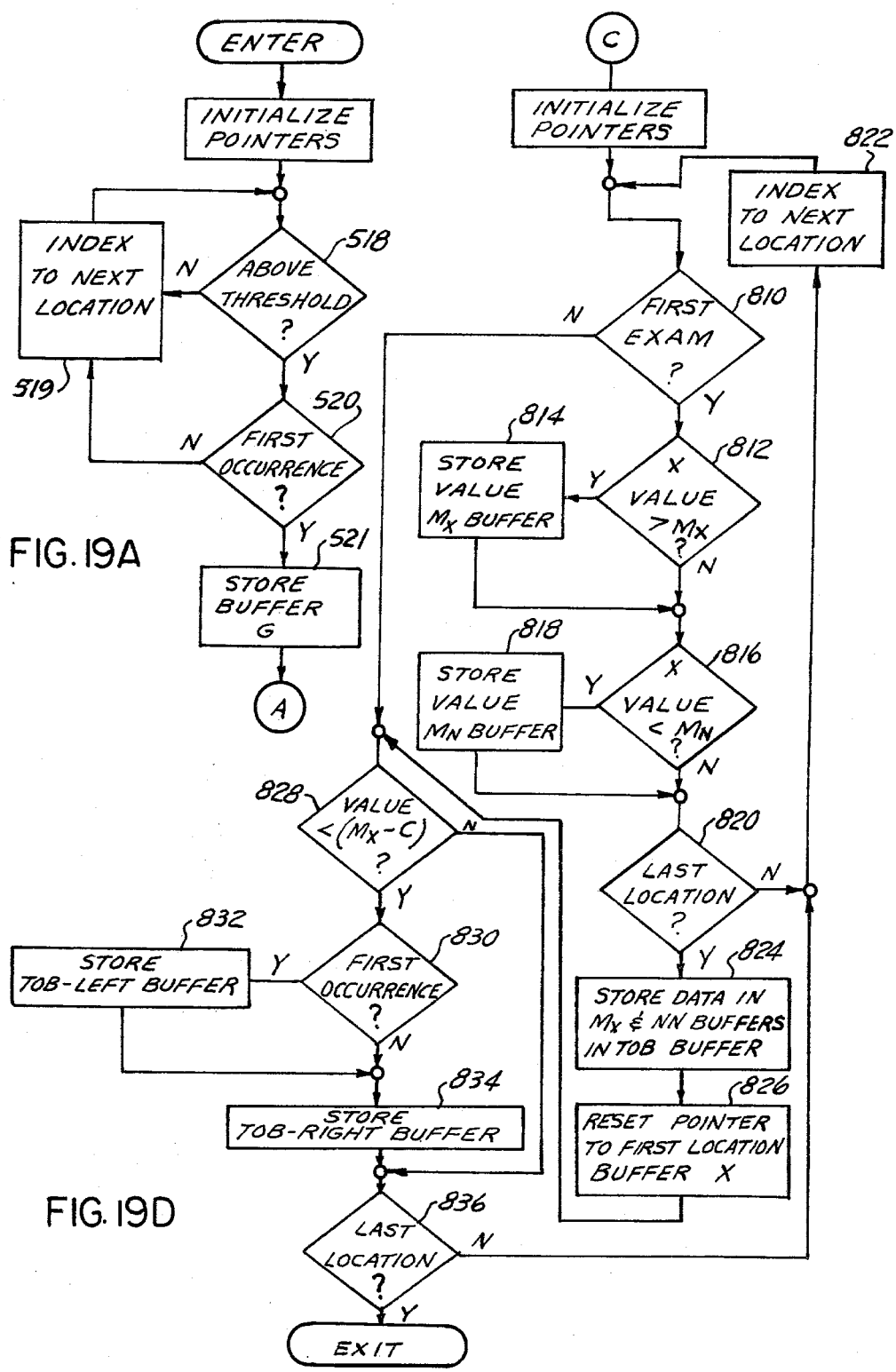

FLAW DATA FORMAT

| PRODUCT P | PRODUCT (TEMPLATE) LENGTH | | FACE OR RIP INDEX | DEFECT INDEX OF ALLOWABLE FLAWS |
| --- | --- | --- | --- | --- |
| | MAX | MIN | | |
| $p$ | $\ell_{T2}$ | $\ell_{T1}$ | F | $D_j$ (1,2------16) |
| | | | | |
| 1 | 84.0 | 84.0 | 3 | Defect $D_j = 2$ |
| 2 | 85.0 | 85.0 | 1 | $D_j = 2$ |
| 3 | 31.0 | 31.0 | 3 | $D_j = 1$ and 2 |
| ⋮ | ⋮ | ⋮ | ⋮ | |
| 11 | 18.0 | 9.1 | 3 | $D_j = 2$ and 3 |
| ⋮ | ⋮ | ⋮ | ⋮ | |
| ⋮ | ⋮ | ⋮ | ⋮ | |
| $p$th | ⋮ | ⋮ | ⋮ | |
| | | | | |

FIG. 26

<u>ORDER ENTRY LIST</u>

SEGMENT BUFFER (a) | $k$ | $s$ | $y_1(s), y_2(s)$ | ---------- |

REMAINDER BUFFER (b) | $k$ | $r$ | $y_1(r), y_2(r)$ | ---------- |

CUT-MARK BUFFER (c) | $k$ | $c$ | $y_1$ | $y_2$ | --- | $y_c$ | ------- |

YIELD BUFFER (d) | $n$ | $n_1$ | $n_2$ | $n_3$ | ----- | $n_p$ |

FIG. 27

EXECUTIVE MODULE

FIG. 31
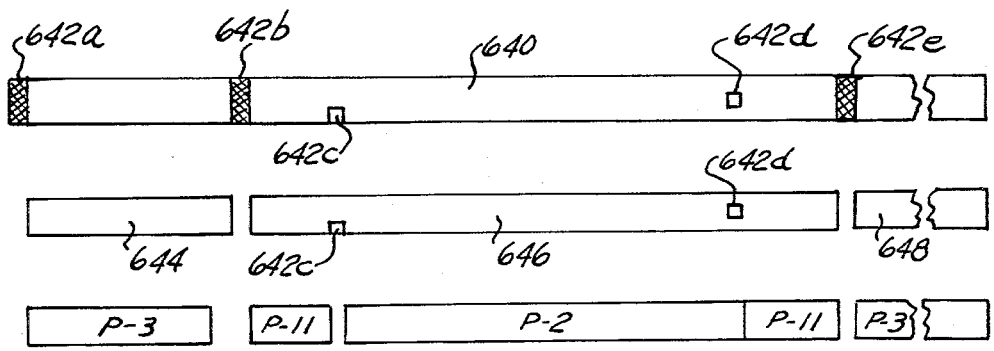
FIG. 32
CONTENT OF FLAW DATA BUFFER
| k | L | W | T | i | X1 | X2 | Y1 | Y2 | di | F |
|---|---|---|---|---|----|----|----|----|----|----|
| 1. | 195.0 | 4.9 | 1.3 | 1 | 0.0 | 4.9 | 0.0 | 4.2 | 16 | 3 |
|  |  |  |  | 2 | 0.0 | 4.9 | 37.0 | 39.1 | 16 | 3 |
|  |  |  |  | 3 | 0.0 | 1.5 | 57.4 | 58.6 | 13 | 3 |
|  |  |  |  | 4 | 1.2 | 2.2 | 140.3 | 141.5 | 13 | 1 |
|  |  |  |  | 5 | 0.0 | 4.9 | 157.1 | 159.1 | 16 | 3 |
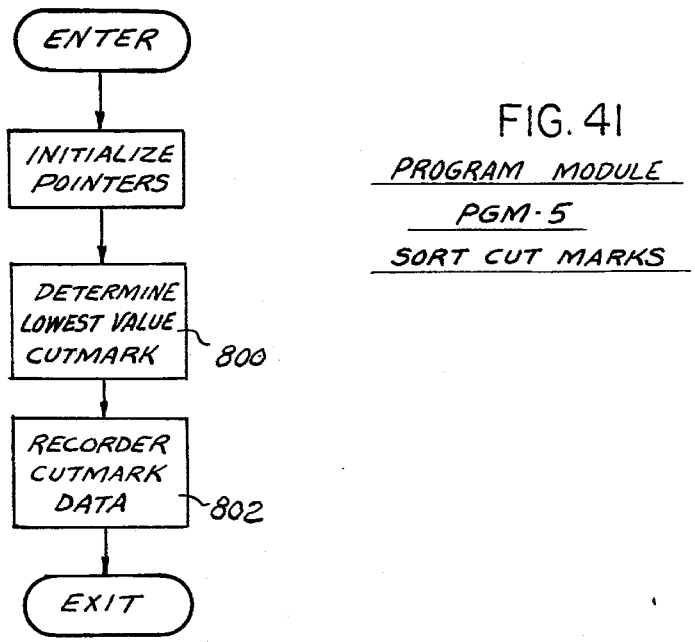
FIG. 41
PROGRAM MODULE
PGM-5
SORT CUT MARKS

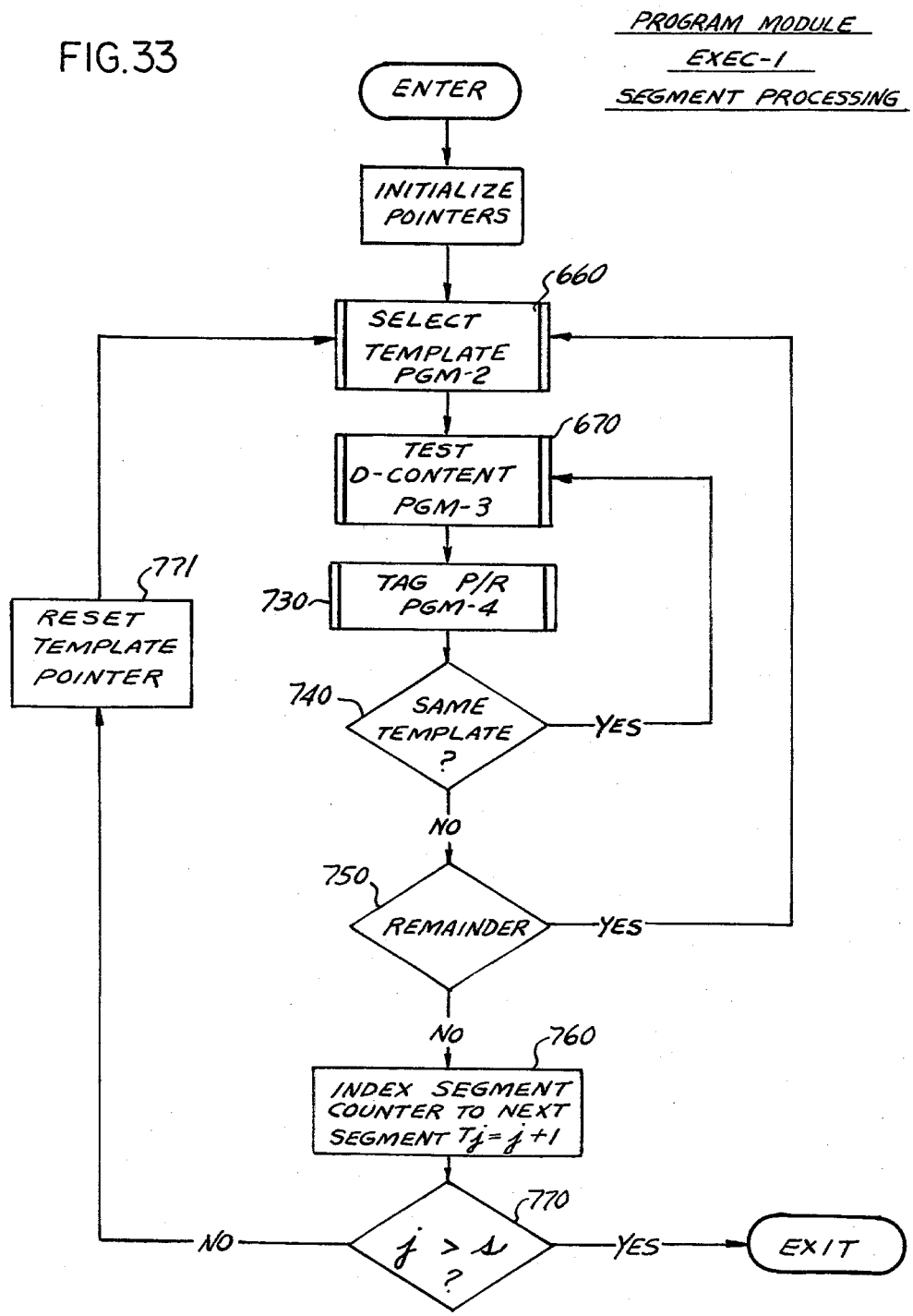

LUMBER INSPECTION AND OPTIMIZATION SYSTEM

CROSS REFERENCE TO OTHER APPLICATIONS

This application is a continuation-in-part of, and contains subject matter disclosed in the applicant's copending application, Ser. No. 933,393 filed Aug. 14, 1978 which is a division of application Ser. No. 818,252 filed July 22, 1977, U.S. Pat. No. 4,149,089, issued Apr. 10, 1979 which is a continuation of the applicant's prior application, Ser. No. 638,116 filed Dec. 5, 1975, now abandoned.

BACKGROUND OF THE INVENTION

1. Field of the Invention

The present invention is generally directed to systems maximizing the utilization of materials having irregular and unpredictable flaws and other defects such as found in forest products, plate glass, sheet metal and the like. The invention is particularly directed to a lumber inspection and optimization system embodying an electro-optical scanner generating data indicative of the location and size of flaws, a man-operated flaw classification device generating data indicative of the flaw class, an order entry device receiving data indicative of the size and quality of the desired product, and an electronic processor generating data indicative of the locations where the inspected piece of lumber is to be cut for optimum product yield.

2. Prior art

The woodworking industries, such as the furniture, millwork and molding plants, are faced with maximizing the utilization of the available lumber. The requirements of the various woodworking industries vary over a considerable range dependent primarily upon their principle output or product. The requirements can range from clear, flaw-free board pieces to pieces which may contain certain classes of imperfections of given sizes. Further, each woodworking plant has requirements for a variety of sizes of board pieces to meet production requirements. The various board pieces are cut from larger boards which come to the plant or factory as unfinished boards. The unfinished boards inherently possess various classes of defects and imperfections, such as tight and loose knots, cracks, checks, splits, bark, stain, pitch pockets and the like. The problem facing each woodworking facility is the analysis of each incoming board to determine how it may be cut to most efficiently meet the production requirements of the particular plant or facility. Typically, this is done by an experienced human inspector who, having knowledge of the size and quality of board pieces required to meet the facility's production need, evaluates each board and makes an on-the-spot determination as to the most efficient way to cut the particular board. This method has limitations particularly when the board is relatively large and the production need complicated and diverse. Under these conditions, the inspector does not get a good overall perspective of the whole board and his evaluation takes place section by section. Production requirements further limit the time the human inspector has to inspect each board. Therefore, his optimization of any given board may be less than desired. Because of these factors, optimization by a human inspector is generally considered to be inefficient and not cost effective.

To overcome this deficiency, the prior art has disclosed a variety of systems to aid or replace the human inspector in identifying and evaluating flaws in forest products. Finlay et al in U.S. Pat. No. 3,120,861 "Method and Apparatus for Identifying and Evaluating Surface Characteristics of Forest Products" (Feb. 11, 1964) discloses a rudimentary system for identifying and evaluating surface characteristics of forest products and is expressly incorporated by reference. The Finlay et al system electro-optically scans the surface of the board to detect the flaws and then either marks the board where it is to be cut or actuates a saw to remove these flaws. This system only locates the flaws along the length axis of the board. Detection of objectionable flaws in the Finlay et al system is determined by the pulse amplitude of the detected flaw and a recurrence on at least three successive scans. A deficiency of this system is that some flaws are difficult to detect by scanning the surface and may go undetected while surface dirt or other surface characteristics, such as an unusually dark grain, may be detected as a flaw resulting in a waste of material.

The concept of utilizing a computer for optimizing the cutting of lumber is introduced by Buss et al in U.S. Pat. No. 3,329,181 "Apparatus and Method for Cutting Assorted Length from Material Having Irregular and Random Defects" (July 4, 1967), the disclosure of which is expressly incorporated by reference. In the Buss et al system, the flaws are manually located by an inspector using an electro-mechanical scanner which generates electrical signals compatible with a computer indicative of the flaw's location. The inspector locates the flaw and marks the coordinates of the upper right-hand corner and lower left-hand corner of an imaginary rectangle encompassing the flaw. The inspector's control also contains a button whereby he may indicate that the indicated flaw is useable in certain inferior grades of stock needed by the plant or facility. The computer stores the size, location and class of defect selected by the inspector and then, in accordance with a predetermined program, determines how the board should be cut for optimum utilization. The computer program contains the size and grade of the board pieces required, as well as the number of each kind of piece necessary to meet its production requirements. Each board piece is weighted in the computation processes according to any of several parameters, such as the monetary value of the particular size and grade, a priority based on the difficulty of obtaining the specific size and grade, as well as the number of pieces required. In addition to determining how the board should be cut, the computer remembers the number of pieces of each kind yielded by that particular board. This information provides an inventory check and also can be input back into the computer program to readjust the arbitrary priority of each type of board to keep the output relatively balanced. Computer programs to perform this type of function are known in the art. Brichard et al in U.S. Pat. No. 3,490,147 "Method for Optimally Cutting Successive Panels in Pieces from a Sheet or Strip" Jan. 20, 1970), the disclosure of which is expressly incorporated by reference, as well as Buss, teach using computers for optimizing the cutting of sheets or strips in accordance with predetermined programs wherein the various sizes and grades have weighted values. The concept for using a computer for optimizing the cutting of lumber for maximum yield is also found in published literature. Typical examples are Englerth and Dummire "Programming for Lumber Yield", *Forest Products Journal*, Vol. 16, No. 9, Sept. 1966—Hallock and Bulgrin, "Tomorrow: Computer Made Sawing Decisions?", *Forest Products Journal*, Vol. 20, No. 9, Sept. 1970—Hafley and Hanson, "Optimum Sequence of Cutting Bills", *Forest Products Journal*, Vol. 23, No. 8, August 1973, each of which are expressly incorporated by reference. These computer programs can be adjusted for maximum monetary yield, maximum useable lumber or maximum yield for specific sizes in predetermined proportions.

The problems of the prior art systems include flaw detection and classification, as well as imparting the required information to the computer in a fast and efficient manner. The disclosed system combines the judgment capabilities of a human inspector with the speed of an electro-optical scanner in a manner to provide the proper information to the computer in a usable form in the most efficient manner.

SUMMARY OF THE INVENTION

The invention is a lumber inspection and optimization system combining the speed of electro-optic scanning for flaw detection and location with a computer for determining the optimum way a board is to be cut for maximum yield per dollar value, lumber utilization, and/or to fulfill the production requirements of a woodworking plant. The system may embody a computer actuated saw to cut the board at the determined locations. The preferred embodiment of the system includes an upstream inspector station, an electro-optical scanner, a flaw processor, a lumber optimization computer, an order entry device and an output station. At the inspector station, a human inspector may enhance a flaw for detection by the electro-optical scanner or may suppress surface markings or other unobjectionable characteristics which the electro-optical scanner would detect as an objectionable flaw. The electro-optical scanner scans opposite sides of the board in a sequentially interlaced scanning pattern to generate scan data indicative of the surface characteristics and the precise location of the flaws on both sides of the board. The electro-optical scanner includes an optical scanner, a data quantizer and a scanner interface to format the scan data into a format acceptable to the computer. The flaw processor receives flaw data from the electro-optical scanner, generates enlarged rectangles about each detected flaw to compensate for defective areas usually surrounding each flaw and then stores the location of edges of the enlarged rectangles in a flaw data buffer. If the order entry list includes pieces of lumber which may have predetermined classes of defects, the inspector station further includes a defect classification device operated by the human inspector which generates data indicative of the approximate location and class of each flaw. This flaw class is subsequently combined with the scan data in the flaw processor and stored in the flaw data buffer. The lumber optimization computer compares the data in the flaw data buffer with the data received from the order entry device and computes, in accordance with a predetermined program, the optimum way in which the board is to be cut. The order entry device enters into the computer the size, priority and classes of permitted flaws for each different piece desired for a particular run, day and/or facility. The output station receives the data from the lumber optimizer computer and either marks the lumber at the locations where it is to be cut or actuates a saw to cut the lumber, as determined by the lumber optimizer computer.

The object of the invention is a lumber inspection and optimization system utilizing the speed and accuracy of electro-optical scanning in combination with inputs from a human inspector to locate and classify the flaws and to optimize the cutting of the lumber in accordance with predetermined board requirements using a mini computer. Another object of the invention is a system in which both sides of the board are contemporaneously scanned and the scan data is quantized to permit rapid and accurate determination of the defects, their type and location. These and other objects will become evident from the accompanying drawings, a reading of the specification and claims.

BRIEF DESCRIPTION OF THE DRAWINGS

FIG. 1 is a block diagram illustrating the basic elements of the disclosed lumber inspection and optimization system.

FIG. 2 is a block diagram illustrating the details of the electro-optical scanner and the flaw classification input devices.

FIG. 8 illustrates the format of the X and Y data bytes.

FIG. 9 illustrates the format of special Y data bytes.

FIG. 10 is a block diagram of the scanner interface.

FIGS. 19A through D are flow diagrams illustrating the program logic for forming the rectangles about each flaw and forming Top of Board buffer.

FIG. 26 is a typical example of order entry list.

FIG. 27 shows the format for the Segment Buffer, Remainder Buffer, Cutmark Buffer and Yield Buffer.

FIG. 31 shows the computer selected products from an actual board.

FIG. 32 is a table showing the content of the flaw data buffer for the board shown in FIG. 31.

FIG. 33 is a flow diagram for program module EXEC1.

FIG. 41 is a flow diagram for reordering cut marks.

DESCRIPTION OF THE PREFERRED EMBODIMENT

Figure 3:
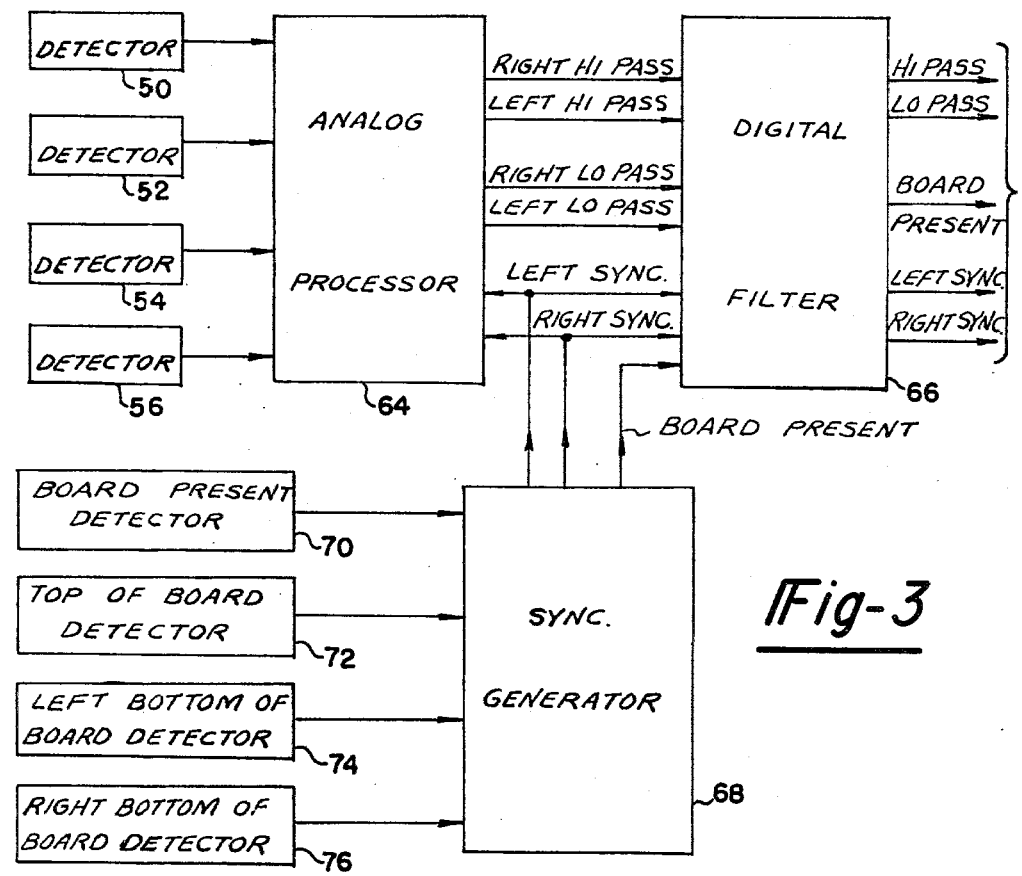
FIG. 3 is a block diagram of the dual quantizer.

A block diagram of the disclosed lumber inspection and optimization system is shown in FIG. 1. The broad arrows show the path of an incoming piece of lumber illustrated as board 10 through the inspection and optimizer system while the narrow lines show the data flow through the system. The lumber inspection and optimizer system comprise an Inspector Station, an Electro-Optical Scanner, a Flaw Processor, an Optimization Computer, an Order Entry Device, and an Output Device. The board 10, by means of a conveyor (not shown) first passes through an Inspector Station 12 where it is inspected by a human inspector who enhances difficult to detect flaws and suppresses surface characteristics which may erroneously be detected by the Electro-Optical Scanner 14 as flaws. The Inspector Station 12 may also embody a defect classification input control which permits the human inspector to classify certain visible flaws. This flaw class information is later transformed to electrical data and stored in the Flaw Processor 16 in the same sequence as detected by the Electro-Optical Scanner 14. After passing through the Inspector Station 12, the board 10 passes through the Electro-Optical Scanner 14 which optically scans both sides of the board and generates scan data indicative of the size of the board, as well as the size and exact location of the flaws. The flaw class data from the Inspector Station 12 and the scan data are processed in the Flaw Processor 16 to generate flaw data which is indicative of the size, the class and the exact location of each flaw. The Flaw Processor 16 also forms enlarged rectangles about each detected flaw in accordance with fixed rules to include in the detected flaw area cross grain and other objectional characteristics which typically surround the flaws.

An order entry list containing the physical descriptions of pieces required for production or needed to fill sales orders is entered by means of an Order Entry Device 20. The physical description of each piece will normally include its size, class of defects allowed when certain classes of defects are permitted, the value and the priority of each piece. The Order Entry Device 20 may be a tape or card reader, a keyboard or any other device capable of transforming an input order into electrical signals compatible with the language of the Optimization Computer 18.

Hereinafter, the term "board" will refer to the rough piece of lumber input into the lumber inspection and optimizing system and "product" will refer to the subparts cut from the board which conforms to items on the order entry list. The order entry list along with the flaw data from the Flaw Processor 16 are input into the Optimization Computer 18 where the utilization of the lumber in the board is maximized in accordance with the optimization program of the computer. The Optimization Computer 18 computes how the board 10 is to be cut and outputs the computed information into the Output Device 22. The Output Device 22 may either mark the board 10 where it is to be cut or alternatively cut the board where directed by the computer. As in the prior art system such as taught by Buss et al in U.S. Pat. No. 3,329,181, the cutting by the Output Device 22 is limited to a cross cut which results in the basic pieces from which the desired product can be obtained by subsequent rip sawing to predetermined widths. The computed optimization information may also be used to generate an inventory on the number of products produced from the inspected board. This information may also update the priority of the individual products on the input order list where priority is at least partially based on the number of products required. These latter procedures are well known and are not considered to be part of the invention.

The block diagram of FIG. 2 shows in greater detail individual elements of the Inspector Station 12 and the Electro-Optical Scanner 14. The Inspector Station 12 comprises an inspector defect classification control such as Keyboard 24, Keyboard Interface 26, Board Position Encoder 27 and Buffer Storage 28. The Board Position Encoder 27 generates encoded signals indicative of a distance measured from the boards leading edge as it is carried by the conveyor past a predetermined point in the Inspector Station 12. The Keyboard 24 has a plurality of keys by means of which the inspector serially designates the class of each flaw as it passes the same predetermined point in the Inspector Station 12. Data indicative of the flaw class from the Keyboard 24 and the signals from the Board Position Encoder 27 are combined in the Keyboard Interface 26 and placed in a format compatible with the computer language. The data from the Keyboard Interface 26 is temporarily stored in a Buffer Storage 28. The data stored in the Buffer Storage 28 is extracted by the Flaw Processor 16 and combined with the flaw data generated by the Electro-Optical Scanner 14 prior to optimizing by the Optimization Computer 18.

In the following discussions involving electro-optical scanning, it will be assumed the board passes through the scanner in the Y direction and is line scanned in an X direction along the surfaces of the board normal to the Y direction. The Electro-Optical Scanner 14 comprises a Laser Light Source 30 generating a focused beam of light. The generated light beam is divided into two spatially separated beams by a Beam Splitter 32 and caused to impinge upon a Rotating Multi-Faceted Mirror 34. One beam is reflected by the Multi-Faceted Mirror 34 to scan the left side of the board 10 by means of a pair of fixed Mirrors 36 and 38, while the other beam is reflected by an alternate face of the rotating Multi-Faceted Mirror 34 to scan the opposite side of the board 10 by a second set of fixed Mirrors 40, 42 and 44. The optical system is arranged to cause the two laser beams to alternately line scan opposite sides of the board along lines from bottom to top, as indicated by the arrows 46 and 48. Because the motion of the board through the scanner is continuous, the line scans on one side of the board interlace the line scans on the other side of the board. The portions of the laser beams reflected by the board are detected by two pairs of Photo Detectors 50 and 52 and 54 and 56, one pair disposed on each side of the board, as shown, to generate analog scan signals. Because the two sides of the board are alternately scanned, the line scan data from the opposite sides of the board are generated in an alternating sequence. The two Photo Detectors in each pair are angularly disposed to each other and to the surface of the board to maximize detection of flaw having depth via detection of their shadows. The analog signals from the two pairs of detectors are sequentially combined and processed by a Dual Quantizer 58. The Dual Quantizer 58 embodies a low frequency pass channel and a high frequency pass channel. The high frequency pass channel quantizes the scan data indicative of narrow flaws, such as season checks and splits, accepting the larger of the signals from the two detectors. The high frequency pass channel has additional digital filtering which simultaneously examines several scan lines and requires a repeated occurrence of a flaw along a line before transmitting high frequency pass flaw signals. This digital filtering suppresses spurious noise which would otherwise pass through the high frequency channel.

The signals from the Dual Quantizer 58 are accepted by the Scanner Interface 60 which encodes the position of the flaws within the line scan, whether the flaw appears on a low pass or high pass channel and whether the scan data was generated upon the occurrence of the scanning light beam entering or leaving a flaw area. In addition, the Scanner Interface 60 combines the scan lines into scan frames and encodes the location of each flaw in the respective scan frame. The Scanner Interface 60 also encodes other conditions, such as end of frame and end of board. This information is transmitted to the Flaw Processor 16 for further data manipulation.

The details of the Dual Quantizer 58 are shown in FIG. 3. The Dual Quantizers 58 comprise an Analog Processor 64 receiving scan data from the Photo Detectors 50 through 56, a Digital Filter 66 and a Synchronization Generator 68 receiving signals from board associate sensors which shall be discussed later. The Analog Processor 64 provides amplification, serial combination of the scan data from the photo detectors, high and low pass frequency filtering, automatic gain control and quantization of the high and low frequency filtered scan data. The quantized high and low frequency scan data hereinafter referred to as "HI-PASS" and "LO-PASS" data from opposite sides of the board are transmitted to the Digital Filter 66 for further processing.

The Synchronization Generator 68 receives signals from four independent sensors and provides various digital clocking, gating and counting functions. A Board Present Detector 70 generates a master gating signal permitting transmission of scan data to the Scanner Interface 60 only when a board is present in the Electro-Optical Scanner 14. Similarly, the Top of Board Detector 72, Left Bottom of Board Detector 74 and Right Bottom of Board Detector 76 are used to generate synchronization signals which gate data to the Scanner Interface 60 and Flaw Processor 16 only when the laser beam is impinging upon the surface of the lumber.

The Digital Filter 66 receives the quantized HI-PASS and LO-PASS scan data from the Analog Processor 64 which are clocked and gated by the synchronization signals from the Synchronization Generator 68. The HI-PASS data is processed through a special purpose Digital Filter to suppress noise and enhance the detection of splits and checks in the board. The filtered HI-PASS and LO-PASS data along with right and left synchronization signals and board present signals are processed in the Scanner Interface 60 which formats the data for subsequent processing in the Flaw Processor 16.

Figure 4:
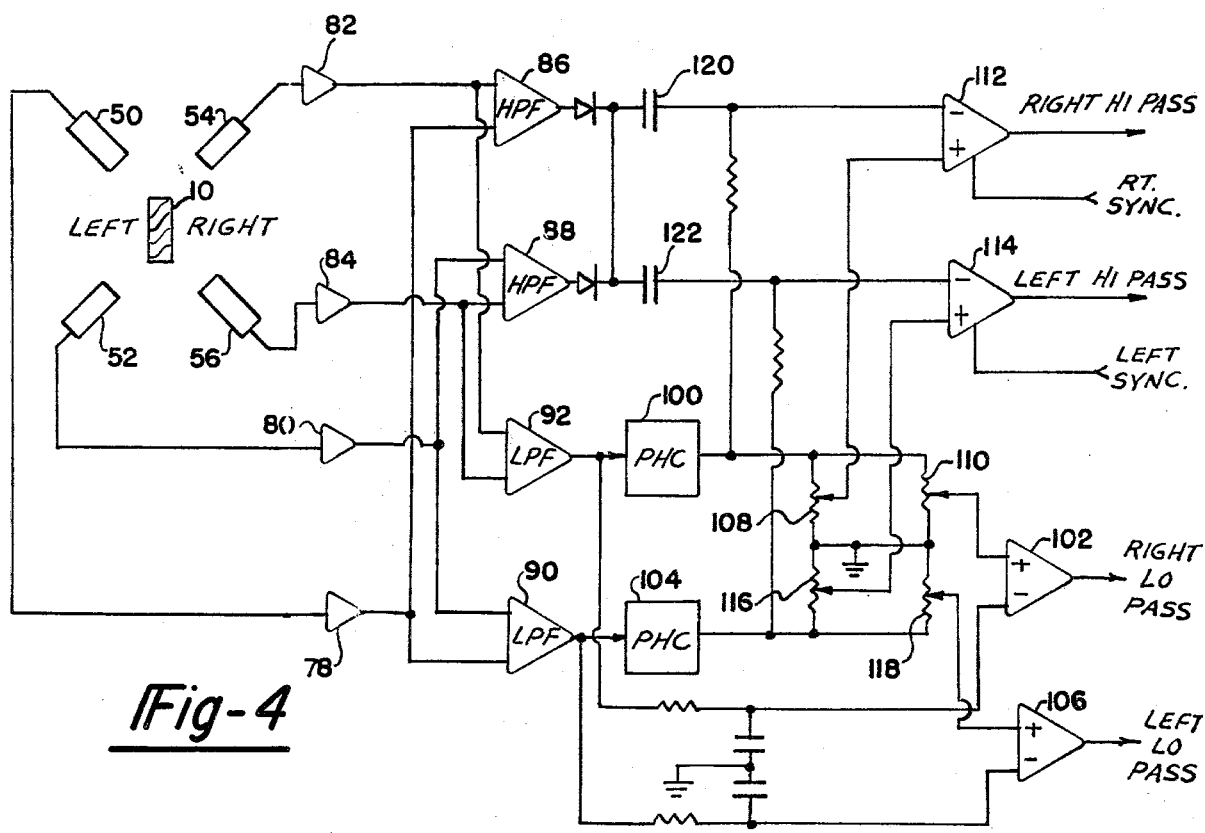
FIG. 4 is an electrical schematic of the analog processor.

The details of the Analog Processor 64 are illustrated in FIG. 4. Referring to FIG. 4, the analog signals from the four Photo Detectors 50 through 56 are amplified by associated preamplifiers 78, 80, 82 and 84. The amplified analog signals are connected to upper HI-PASS Filter (HPF) 86, lower HI-PASS Filter (HPF) 88, left LO-PASS Filter (LPF) 90 and Right LO-PASS Filter (LPF) 92.

The output of the Right LO-PASS Filter 92 is transmitted to a Right LO-PASS Peak Holding Circuit (PHC) 100 and the Right LO-PASS Comparator 102. The output of the Left LO-PASS Filter 90 is applied to Left LO-PASS Peak Holding Circuit 104 and Left LO-PASS Comparator 106. The output of the Right LO-PASS Peak Holding Circuit 100 is applied to a pair of Potentiometers 108 and 110. The opposite terminals of the two potentiometers are connected to ground. The wiper of Potentiometer 108 is connected to the positive input of Right HI-PASS Comparator 112. The wiper of Potentiometer 110 is connected to the positive input of Right LO-PASS Comparator 102. The output of Right LO-PASS Peak Holding Circuit 100 is also applied to the negative terminal of the Comparator 112. The output of Left LO-PASS Peak Holding Circuit 104 is applied to the input of Comparator 114 and to a pair of Potentiometers 116 and 118. The wiper of Potentiometer 118 is connected to the positive input of Left LO-PASS Comparator 106 and the wiper of Potentiometer 116 is connected to the positive input of Comparator 114. The output of upper HI-PASS Filter 86 and lower HI-PASS Filter 88 are "OR'ed" to accept the larger of the signals from the Upper and Lower photo detectors and are capacitor coupled to Comparator 112 and 114 by means of Capacitors 120 and 122.

The operation of the Analog Processor 64 is as follows: During the period when the laser beam is scanning the left surface of the board 10, the Photo Detector 50 generates an analog signal which is amplified by Preamplifier 78 and is communicated to the Upper HI-PASS Filter 86 and to the Left LO-PASS Filter 90. In like manner, a Photo Detector 52 also generates a comparable analog signal which is amplified by Preamplifier 80 and is communicated to Lower HI-PASS Filter 88 and to Left LO-PASS filter 90. The Left LO-PASS Filter 90 removes the high frequency components of the analog signals from the detector and generates a LO-PASS signal which is a sum of the low frequency components of the two input analog signals. The LO-PASS signal is input into the Peak Holding Circuit 104 which generates a signal indicative of the peak intensity of the LO-PASS signal received from Detectors 50 and 52. The output signal from the Peak Holding Circuit 104 is applied to the negative input of the Comparator 114. This signal is also applied to Potentiometers 116 and 118 acting as signal dividers. The signal appearing at the wiper of Potentiometer 116 is used as the AGC reference potential for Comparator 114. The signal at the wiper of Potentiometer 118 is used as the AGC reference potential input for the Left LO-PASS Comparator 106.

The high frequency component of the analog signal of Photo Detector 50 is passed through Filter 86. The high frequency (HI-PASS) output of the Filter 86 is communicated to the Left HI-PASS Comparator 114 by means of Capacitor 122. The HI-PASS signal generated is a negative signal which overcomes the bias potential of the Peak Holding Circuit 104 and causes Comparator 114 to produce a quantized HI-PASS signal. The left sync signal from the Sync Generator 68 gates Comparator 114 so that it is operative only when the left side of the board is being scanned. In a comparable manner, the analog signal from Detector 52 is applied through Preamplifier 80 to the HI-PASS Filter 88 and the LO-PASS Filter 90. The high frequency components of the analog signal from Detector 52 is communicated to Comparator 114 through Lower HI-PASS Filter 88 and Capacitor 122. The low frequency component of the analog signal is passed by Filter 90 to Comparator 106 which generates a LO-PASS signal whenever the low frequency component is more negative than the bias potential produced at the wiper of Potentiometer 118. The operation of the Right HI-PASS and Right LO-PASS sections of the Analog Processor 64 are identical to the operation discussed with respect to Left HI-PASS and Left LO-PASS sections of the Analog Processor and need not be repeated for an understanding of the operation of the circuit.

Figure 5:
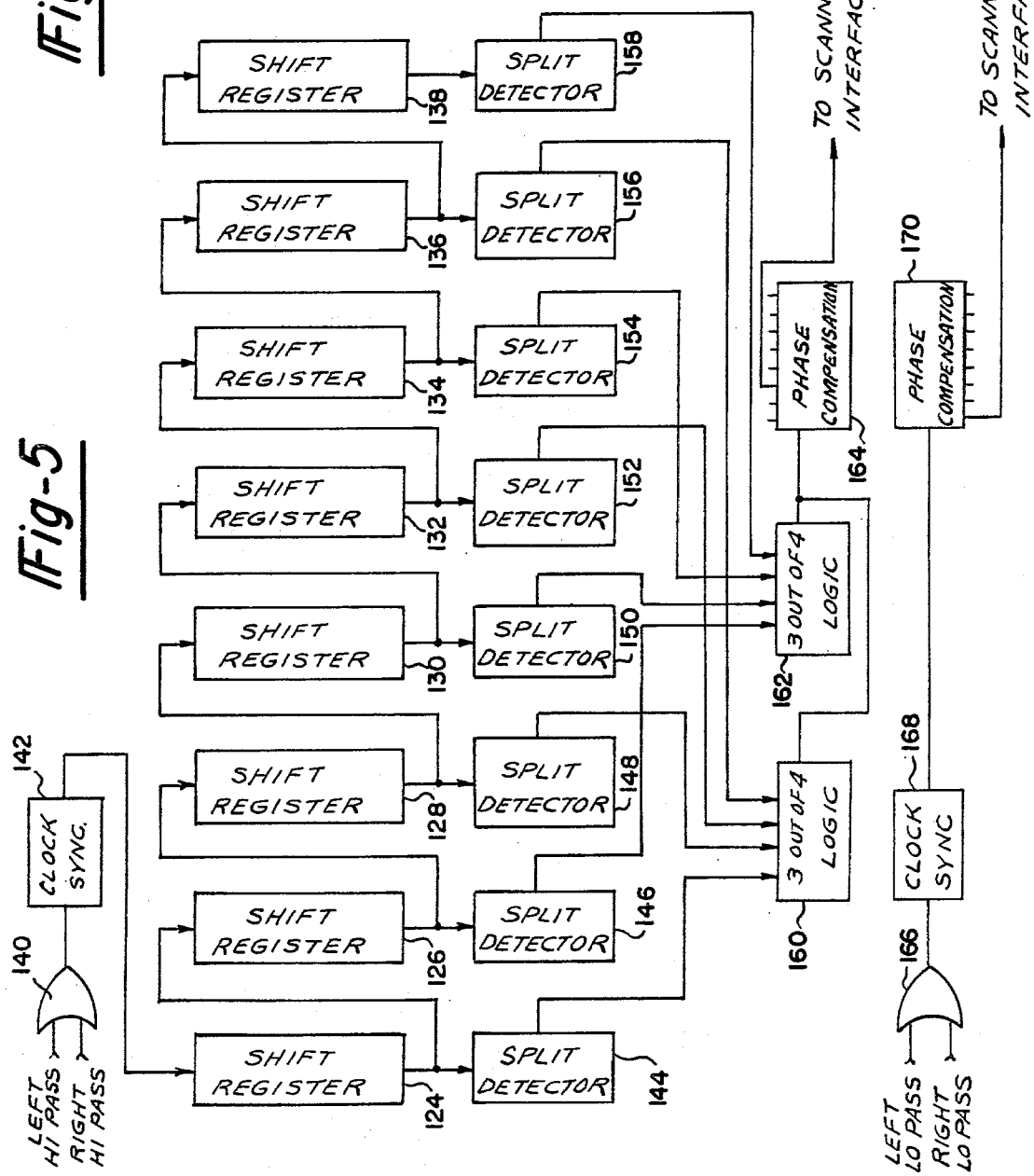
FIG. 5 is an electrical schematic of the digital filter.

The details of the Digital Filter 66 are illustrated in FIG. 5. The right and left HI-PASS signals from the Analog Processor 64 are alternately entered into a set of eight 256 bit Shift Registers 124 through 138 by means of OR Gate 140 and Clock Synchronization Circuit 142 which converts the synchronous HI-PASS comparator data to clocksynchronous digital data. The eight shift registers are connected in series and each register holds exactly one scan line of digital HI-PASS data. Four consecutive scan lines from one side of the board are stored in four alternate shift registers 124, 128, 132, and 136 and four consecutive scan lines from the other side of the board are stored in shift registers 126, 130, 134, and 138 inbetween the four registers storing data from the opposite side of the board.

Eight Split Detector Circuits 144 through 158 observe the data pattern at the end of each 256 bit register and generate a signal when the data pattern at the end of the associated 256 bit register is indicative of a split. Three-out-of-four Logic Circuits 160 and 162 receive signals from the alternating split detector circuits, as shown, and pass HI-PASS signals when at least three out of four associated split detector circuits are generating a signal indicative of a split. The output signal from the three-out-of-four Logic Circuits 160 and 162 are input into a Phase Compensation Circuit 164 prior to being output to the Scanner Interface 60.

The right and left LO-PASS data are serially combined by OR Gate 166 and converted to digital form by Clock Synchronization Circuit 168. The digital LO-PASS data is input to a Phase Compensation Circuit 170 prior to being output to the Scanner Interface 60. The Phase Compensation Circuits 164 and 170 re-establish the proper phase relationship between the digital HI-PASS and LO-PASS data for subsequent manipulation in the Scanner Interface 60, Flaw Processor 16 and Optimization Computer 18.

Figure 6:
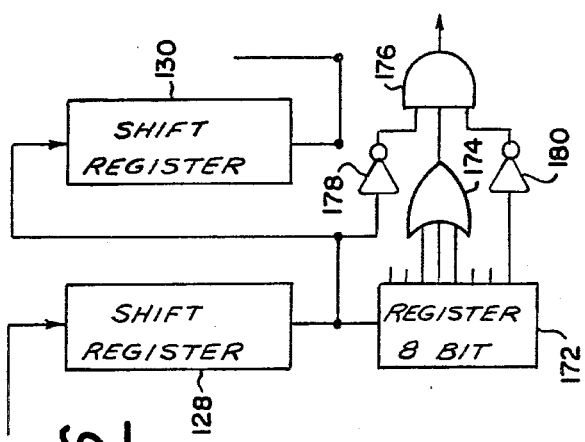
FIG. 6 is an electrical schematic of the split detector.

The details of the Split Detector Circuits 144 through 158 are illustrated in FIG. 6. Each Split Detector Circuit comprises an Eight Bit Register 172 holding the last eight bits of data output from the associated 256 Bit Shift Register, as illustrated. An OR Gate 174 monitors the third, fourth and fifth bit locations in the Register 172 and outputs a signal when a high pass data bit is present in one or more of these three bit locations. The output of OR Gate 174 is input into an AND Gate 176 along with the outputs from Inverters 178 and 180 transmitting the bit data disposed three bit locations either side of the locations monitored by the OR Gate 174. If the output of OR Gate 174 indicates a flaw and simultaneously the outputs of Inverters 178 and 180 indicate no flaw, then a narrow defect is present. The output signal of AND Gate 176 is indicative that the defect is narrow, such as a crack, split or check.

Figure 7:
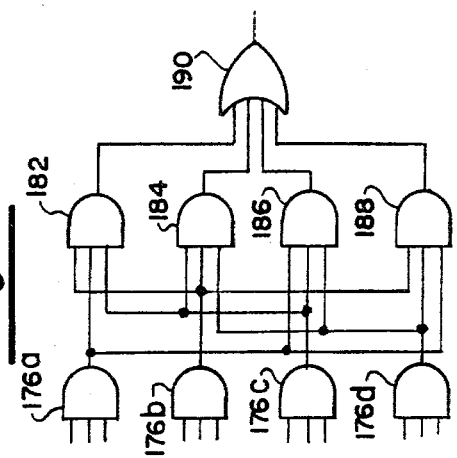
FIG. 7 is an electrical schematic of the three-out-of-four logic.

The details of the three-out-of-four Logic 160 and 162 are shown in FIG. 7. The outputs from the four AND Gates 176a through 176d associated with one side of a board are input to a like set of AND Gates 182 through 188. The first AND Gate 176a has its output connected to input gates of AND Gates 182, 186 and 188. The second AND Gate 176b has its output connected to inputs of AND Gates 182, 184 and 188 and, likewise, the two other AND Gates 176c and 176d have their outputs connected to input gates of three different AND Gates, as shown. The output of the AND Gates 182 through 188 are connected to OR Gate 190.

The operation of the three out of four Logic Circuits (160 and 162) is straight forward. When defect signals are present on all four AND Gates 176a through 176d, all of the AND Gates 182 through 188 output a defect signal and OR Gate 190 generates a signal indicative of a split or check. When only three of the four AND Gates 176a through 176d output a defect present signal, only one of the AND Gates 182 through 188 will output a defect signal to OR Gate 190. However, the OR Gate 190 will still generate a defect present signal. If more than one of the AND Gates 176 does not output a defect signal, then all of the AND Gates 182 through 188 are inhibited and none produce a defect present signal. When none of the AND Gates have a defect present signal, OR Gate 190 will not produce a HI-PASS defect signal.

Referring again to FIG. 2, the Scanner Interface 60 formats the output data from the Dual Quantizer 58 in a form suitable for entry into the Flaw Processor 16. The specific functions of the Scanner Interface 60 are to generate specifically coded eight bit data bytes indicative of various occurrences during the scan processes and to subdivide the scan data into a plurality of discrete data frames to facilitate processing and reduce storage requirements for subsequent data manipulation. Each data frame comprises the data from a predetermined number of scan lines which represent a predetermined section of the board having a specific length. The flaw data from the Scanner Interface 60 is input to the Flaw Processor 16 on a frame-by-frame basis to permit flaw processing, such as analysis of the flaws and enlargement of the flaw area to proceed while scanning of subsequent sections of the board are still in progress.

The laser beam scans the board from bottom to top in a direction previously designated as the X axis and the board passes through the scanner along the Y axis. In accordance with this rationale, The Scanner Interface 60 generates X data bytes indicative of occurrences during the line scan along the X axis and Y data bytes at the end of each scan line, at the end of each frame, and at the end of the board indicative of longitudinal data along the Y axis. Eight bit X data bytes are generated upon each of the following occurrences:

(1) a signal from the Dual Quantizer 58 indicating that laser beam has entered a HI-PASS flaw region;

(2) a signal from the Dual Quantizer 58 indicating that laser beam has left a HI-PASS flaw region;

(3) a signal from the Dual Quantizer 58 indicating that laser beam has entered a LO-PASS flaw region;

(4) a signal from the Dual Quantizer 58 indicating that laser beam has left a LO-PASS flaw region; and (5) a termination of the sync signals. In a like manner, eight bit Y data bytes are generated upon each of the following occurrences:

(1) The end of each line scan line;

(2) the end of each frame;

(3) the end of the board.

The format of the eight bit X data and Y data bytes are illustrated in FIG. 8. The first bit designates whether the data byte is an X byte or Y byte. A logic "0" is indicative of an X byte and a logic "1" is indicative of the Y byte. The second bit of an X byte designates whether the data is HI-PASS (logic 0) indicative of a check, crack or split or LO-PASS (logic 1) indicative of a larger flaw, such as a knot or other defect. The third bit of the X byte designates whether the scanning beam is entering (logic 0) or leaving (logic 1) the flaw. The remaining five bits give the X location of the occurrence. The last LO-PASS entering X byte in each scan line is the top of the board signal.

The format of the Y byte data is slightly different than that of the X byte data. The second bit of the Y byte is indicative of the absence (logic 0) or presence (logic 1) of HI-PASS data during that entire scan line and the third bit of Y byte is indicative of the absence (logic 0) or presence (logic 1) of LO-PASS data during the entire scan line. The last five bits of the Y byte give the Y location of the scan line in the given frame.

The details of the Scanner Interface 60 are described with reference to the block diagram illustrated in FIG. 10. The board present; left (L sync), and right (R sync) signals from the Dual Quantizer 58 are input to a Sync Processor 200 which generates counter enable, counter clear, and end of board (EOB) signals for the X, Y and frame counters of block 202. The X counter counts clock pulses and generates five bit X locations for the X bytes, as a function of the position of the laser beam as it scans across the board in a direction approximately parallel to the X axis. The Y counter counts the sync signals and generates five bit location for the Y bytes indicative of the predetermined distance along the Y axis of the board within each frame. The frame counter is incremented by the Y counter after a predetermined number of scan lines have been counted. The five bit X and Y location signals are input directly into a Multiplexer 204 and the signal indicative of the end of a frame from the Y counter is input to a Fixed Code Generator 206 which generates the special code shown on FIG. 9 as indicative of the end of a frame. The Fixed Code Generator 206 also responds to the end of board (EOB) signal and generates the special code shown in FIG. 9 as indicative of the end of the board.

The digital HI-PASS and LO-PASS signals from the Dual Quantizer 58 along with Sync signals from the Sync Processor 200 are input to Quantizer Processor 208 which generates the data bit indicative of whether the occurrence is from the HI-PASS or LO-PASS channel and whether the occurrence represents entering or leaving data, as required by the eight bit X byte format illustrated in FIG. 8. The data bits from the Quantizer Processor 208 are also input to the Multiplexer 204 where it is combined with the appropriate location information generated by the X counter to produce an X byte.

The data bytes generated by the Multiplexer 204 are stored serially in a first-in-first-out (FIFO) Buffer 210. The purpose of this buffer is to temporarily store the data, if it is generated at a rate too fast to be read directly into the Flaw Processor 16.

The Scanner Interface 60 also includes an Address Generator 212 which generates memory addresses for the data bytes in the Flaw Processor 16 and addresses for reading byte data from the FIFO Buffer 210 into a Duplexer 214. The Duplexer 214 alternately transmits sequential memory addresses from the Address Generator 212 and data bytes from the FIFO Buffer 219 to the Flaw Processor 16.

Circuits for performing the functions described with reference to the blocks in the block diagram illustrated in FIG. 10 are sufficiently well known and detailed circuit diagrams are not required for a complete understanding of the Scanner Interface 60.

The Flaw Processor 16, as well as the Optimization Computer 18, may be individual hard wired or soft wired components having appropriate logic and storage capabilities or they may alternatively be embodied in a mini computer programmed to perform both desired functions. Because the mini computer option provides the maximum flexibility and adaptability to the many diverse applications for this type of a system, the preferred embodiment of the Flaw Processor 16 and Optimization Computer 18 is described in terms of a mini computer having the requisite storage facilities and programmed to perform both the flaw processing and optimization functions. A GTE IS-1000 manufactured by GTE Information Systems, Inc. of Fullerton, California has been used in the development of the Lumber Optimization system and is an example of one such mini computer capable of performing the desired functions.

Figure 11:
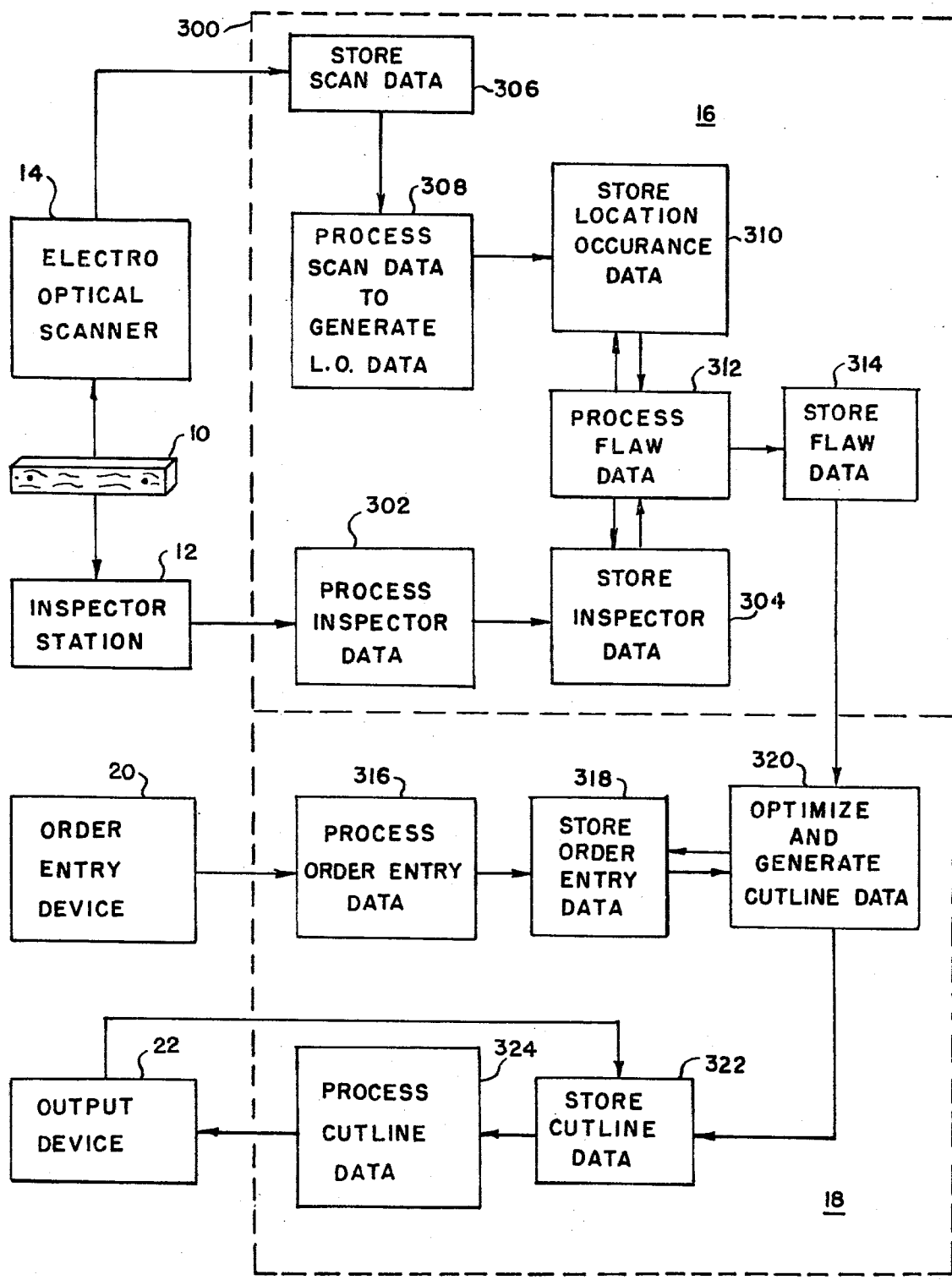
FIG. 11 is a block diagram illustrating the primary operational functions of the mini computer.

The block diagram of FIG. 11 shows the primary operational functions of the mini computer 300 and its interrelationship to the external hardware. The board 10 first passes the Inspector Station 12 where a human inspector, by means of his keyboard, generates flaw class data indicative of the defect category of the flaws on the surface of the board in the order in which they will be detected by the Electro-Optical Scanner 14, as well as identifying the board, by number (k). The data generated at the Inspector Station 12 is processed in the computer as indicated by block 302 and temporarily stored in the inspector data buffer indicated by block 304.

After passing through the Inspector Station 12, the board 10 passes through the Electro-Optical Scanner 14 which generates scan data in the form of X and Y bytes indicative of the size, shape and location of the flaws, as well as the special end of frame and end of board Y bytes. As previously discussed, the scan data from the Electro-Optical Scanner 14 is temporarily stored in the mini computer in a Data Buffer indicated by block 306 on a frame-by-frame basis. Each frame of scan data in the Data Buffer 306 is serially processed, as shown by block 308, to generate location occurrence data indicative of the location of the edges of the flaws and the location of the top of the board for each frame. The location occurrence (LO) data is temporarily stored in location occurrence buffers, illustrated by block 310. The computer then generates flaw data by forming an enlarged rectangle about each flaw. The coordinates of the enlarged rectangle about each flaw are combined, as indicated by block 312, with the inspector flaw class data from the inspector data buffer 304 and the combined data stored in a flaw buffer, as indicated by block 314.

The order entry information is input to the computer through the Order Entry Device 20. The computer processes the order entry data, as shown by block 316, to form an order entry list, listing in the order of priority a description of each product. The order entry list is stored in an order entry list buffer illustrated by block 318. The computer then optimizes the utilization of the board by comparing the sections of the board, as determined from the data contained in the flaw buffer 314 with the type and size of products contained on the order entry list buffer 318 and generates cut line data indicative of where the board is to be cut to produce the optimum product yield, as indicated by block 320.

The cut line data indicative of the locations where the board is to be cut are stored in a cut line buffer, illustrated by block 322, prior to being processed into a format useable by the Output Device 22. When the board is placed in the Output Device 22, the cut line buffer is interrogated and the cut line data is processed, as indicated by block 324, into a format acceptable by the Output Device 22 to either mark or cut a board in accordance with processed cut line data.

Figure 12:
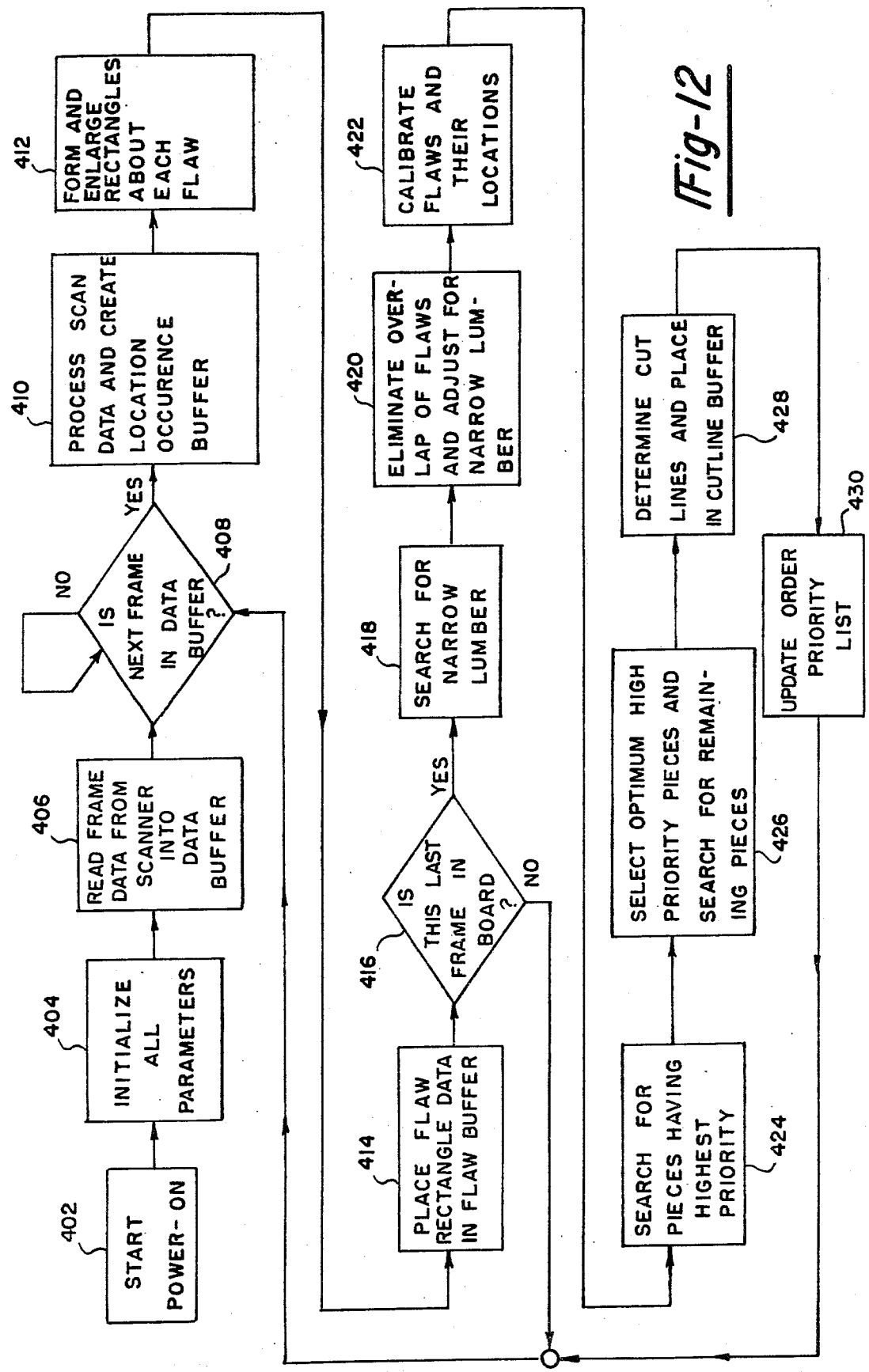
FIG. 12 is a flow diagram of the data in the mini computer.

A flow diagram of the computer program is shown in FIG. 12 while FIGS. 13, 14, 15, 16 and 17 illustrate the five interrupt subroutines of the computer program. FIGS. 18 through 23 illustrate, in greater detail, the process and logic flow of six functions shown in FIG. 12 in particular blocks 410, 412, 418, 420 and 422. FIGS. 24 through 40 further illustrate the specifics of the optimization process shown in blocks 424, 426 and 428.

Referring to FIG. 12, the program is initiated by turning "ON" the system power, as indicated by block 402 and the initialization of the system parameters as indicated by block 404. During the initializing process, the system is placed in a wait status until warmed up and ready. When the system is ready, a board is placed on the conveyor and the Electro-Optical Scanner 14 generates sequential frames of scan data, as previously discussed. Frames of scan data from the Electro-Optical Scanner 14 are sequentially read into the data buffer, as indicated by block 406. After a complete frame of data has been read into the data buffer 406, the scan data is processed, block 410, to create a location occurrence buffer. Each storage location in the location occurrence buffer corresponds to one of 32 locations of the X and Y data bytes. Each storage location acts as a counter. Whenever flaw data occurs at one of the 32 locations, the corresponding counter is incremented. Location occurrence buffers are formed for:

| Byte | Description |
| --- | --- |
| X | HI-PASS Entering |
| X | HI-PASS Leaving |
| X | LO-PASS Entering |
| X | LO-PASS Leaving |
| X | Top Of Board |
| Y | HI-PASS Present |
| Y | LO-PASS Present |

The flaw processing portion of the program indicated by block 412 forms an enlarged rectangle about each flaw in accordance with a predetermined set of rules. For example, if the flow is HI-PASS data indicative of a crack or a check, the flaw processing rule for this type of flaw may require that one inch be added to the beginning and to the end of the flaw data generated by the scanner and that the width of the flaw be increased by one tenth of an inch. However, if the flaw data is LO-PASS data, a different set of rules would apply. The enlargement rules for the LO-PASS data may also differ from one type of flaw to another depending upon whether the width of the flaw is greater than its height or vice versa. The difference in the way this data is handled is intended to eliminate during optimization various types of defects, such as cross grain, wood darkening and other defects which usually surround the larger flaws. There also may be other rules relative to the flaw processing based on whether the flaw occurs at the beginning or the end of the frame data, etc. These rules also provide for continuity of a flaw which extends between two adjacent data frames. After the flaw processing of the board is completed, the flaw data buffer 414 contains the total number of flaws found along the whole length of the board. The last frame logic 416 responds to the Y byte data indicative of the end of the board and determines if the last frame entered into the flaw buffer is or is not the last frame of the board. If the frame is not the last frame of the board, then the next frame is entered into the location occurrence buffer 410 as shown in block 408. After the data from the last frame are placed in the flowdata buffer, the optimization portion of a program is initiated. The first portion of the optimization program is the search for narrow lumber, as indicated by block 418. This process selects a nominal board width based on the greatest top of board value found in any frame of that board. After the nominal board width is selected, a narrow lumber flaw is then created for the top of board values in each frame having values less than the nominal board width by a predetermined amount. The next function of the optimization program is to eliminate the overlap of the flaws in the flaw buffer and adjust the program for the narrow lumber, as indicated by block 420. The next step, as indicated by block 422, is the calibration of the flaws and their locations on the board. The calibration process converts the location of the flaws and the dimensions of the board to conventional units of measure, such as inches in the English system or centimeters in the Metric system and also corrects for errors in the speed of the conveyor. After having calibrated the dimensions of the board and the location of the flaws, the optimization program searches for products in the stored order entry list having the highest priority as indicated in block 424. The program first selects products having the highest priorities and then searches for the products having lower priorities, as indicated in block 426. After the search has been completed, the cut lines are determined and data indicative of the cut line locations is placed in the cut line buffer, block 428. Having completed the optimization of the board, the program may then check for new entries to the priority list and updates the order priority list block 430, prior to initiating processing data from the next board.

Figure 13:
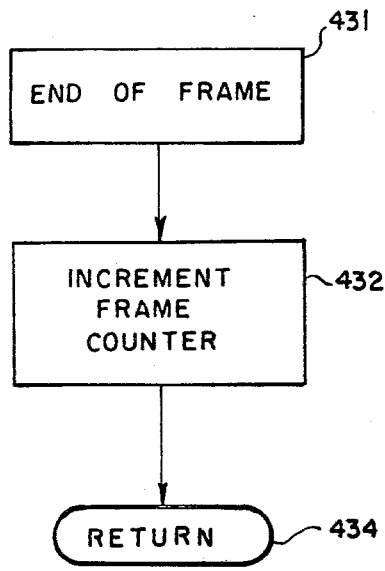
FIG. 13 is a flow diagram of the end of frame interrupt.

End of frame interrupt subroutine of FIG. 13 is executed at the end of each frame. An input channel access is enabled upon program start up and accepts scan data as the board passes through the scanner. The scan data is generated frame-by-frame and an interrupt 431 is produced at the end of each frame. The end of frame interrupt subroutine then increments a frame counter, resets the interrupt system to prepare for the next interrupt 432 and returns control 434 to the interrupted program. The program could be interrupted either during the processing of a previous frame of data, while waiting for the interrupt, or during optimization of a previous board.

Figure 14:
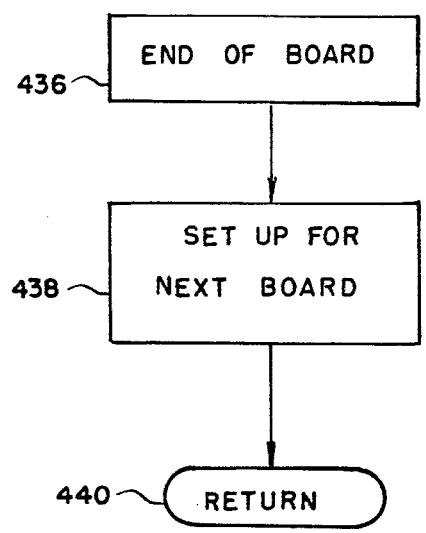
FIG. 14 is a flow diagram of the end of board interrupt.

The end of the board interrupt subroutine, FIG. 14 is executed at the end of the board. When the board leaves the scanner, an end of board signal 436 is generated which increments a board counter, sets up the system to receive data from a new board 438 and returns the control to the interrupted program 440.

Figure 15:
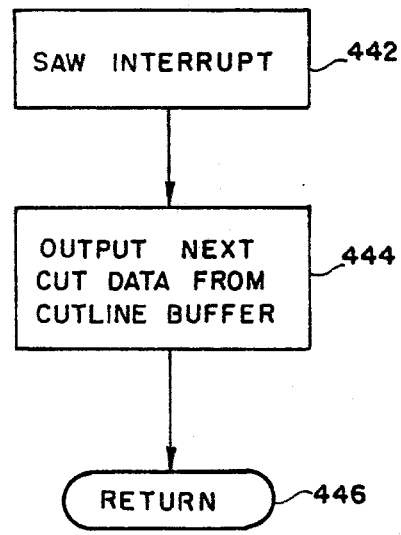
FIG. 15 is a flow diagram of the saw interrupt.

A saw interrupt 442 is generated when the presence of a board is detected at the output device. The saw interrupt subroutine, FIG. 15, is then executed and outputs cut line data 444 to the output device 22 beginning at board dimension zero. As each cut is made or marked, an additional interrupt is generated and new cut line data is output until no further cut line data is left in the cut line buffer. When the data in the cut line buffer is exhausted, the interrupt subroutine generates a return signal 446 indicative of finishing cutting. The next saw interrupt will then occur when the presence of a new board is detected at the output device.

Figure 16:
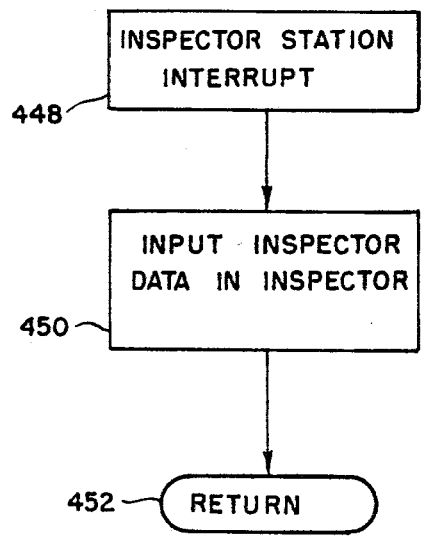
FIG. 16 is a flow diagram of the inspector station interrupt.

The inspector station interrupt subroutine, FIG. 16, is executed each time the inspector enters the flaw class data by a means of his keyboard. The inspector station interrupt 448 inputs the data 450 from the Keyboard 24 and Board Position Encoder 27 into the inspector data Buffer Storage 28. After the flaw class data is entered, the subroutine returns control back to the program 452.

Figure 17:
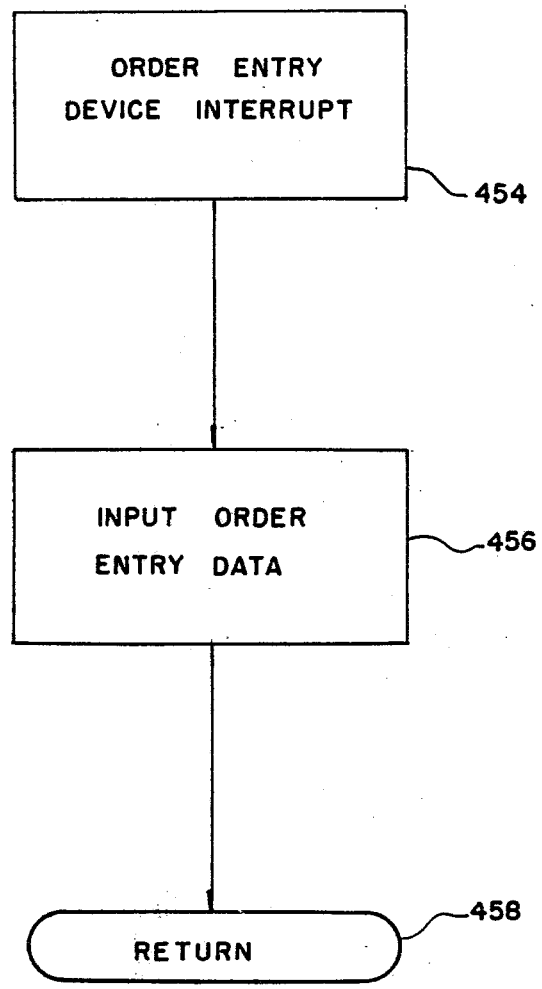
FIG. 17 is a flow diagram of the order entry device interrupt.

An order entry interrupt is generated whenever new order entry data is entered into the order entry device as shown on FIG. 17. The order entry interrupt 454 interrogates the order entry device and inputs 456 the new order entry data. The control is then returned as indicated by block 458 to the program and processing of the current board is resumed. The new order entry data is temporarily stored until the processing of the current board is completed. After completing the processing of each board, the program automatically interrogates the buffer storing the new order entry data, and updates the priority list for the processing of the next board with the new data.

As indicated in the discussion of the prior art, computer programs for the inspection and optimization of the use of lumber are in existence both in printed publications and in issued patents. It is believed that those skilled in the art can modify the teachings of these programs to fulfill the requirements of specific lumber processing systems or use the teaching of the prior art to develop new computer programs. The following discussion describes the specific computer program, logic, and algorithms used in the flow diagram of FIG. 12. In particular, the program logic flow and algorithms used to process the scan data to create Location of Occurrence Buffers (410), to form and enlarge the rectangles about each flaw (412), to search for narrow lumber (418), to eliminate overlap of flaws (420), to calibrate flaws and their locations (422), and to optimize lumber utilization (424, 426) and to determine the cut lines 428.

The Scanner Interface 60, as previously noted, precodes the scan data prior to its being input to the Flaw Processor 16 so that subsequent data manipulation is significantly simplified. This pre-coded data has the byte format shown in FIG. 8 and is stored in the storage buffer, block 406.

Figure 18:
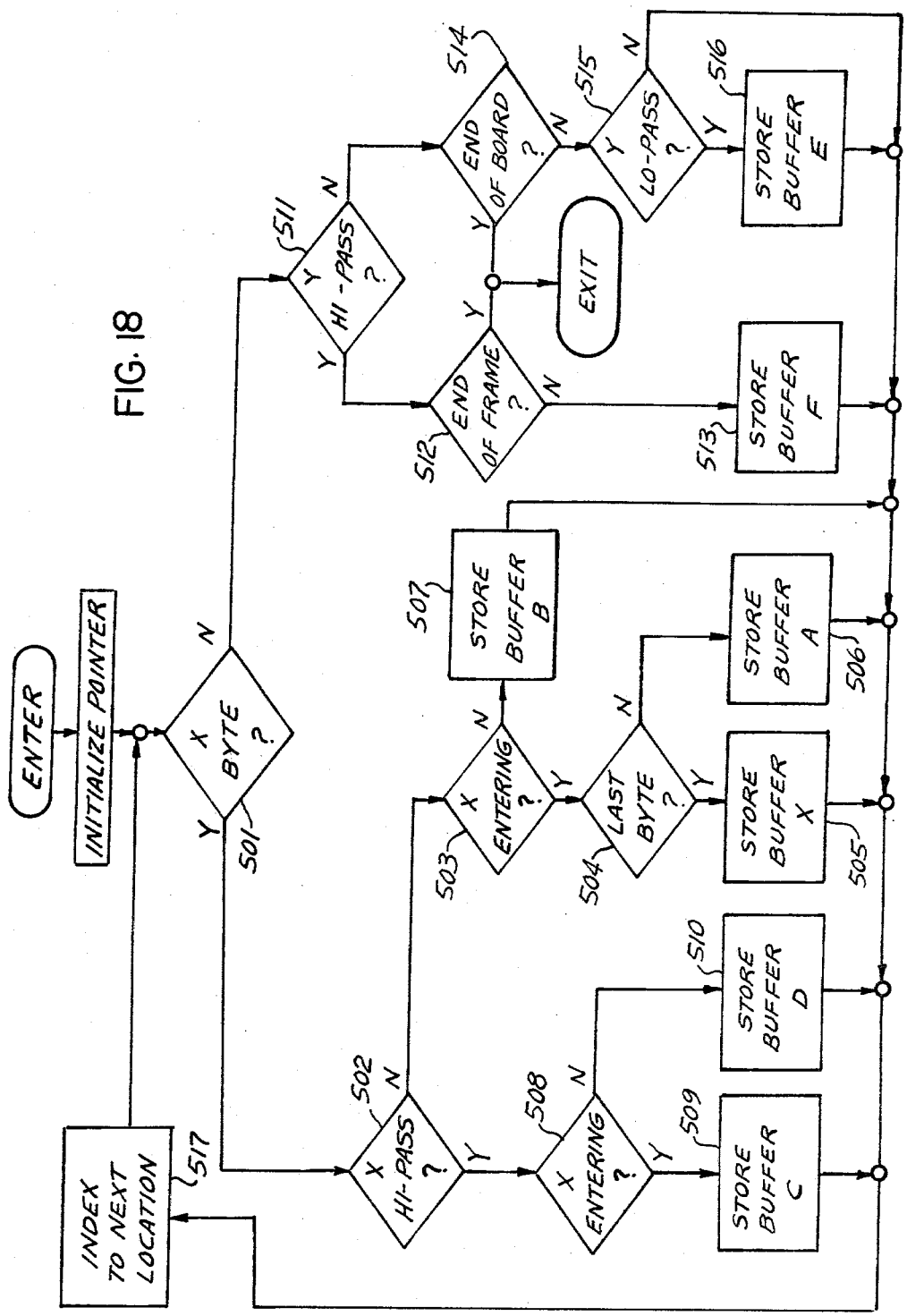
FIG. 18 is a flow diagram illustrating the formation of the location of occurrence buffer data.

The details of the process for forming the location of occurrence buffer (410) are shown in FIG. 18.

Referring to FIG. 18, the program for forming the location of occurrence buffer is entered and the pointers initialized as indicated. The first bit of each data byte received from the scanner and stored in the data buffer is analyzed in block 501 to determine if the data is an X or Y byte. If the data is an X byte, the second bit is analyzed in block 502 to determine if the byte contains HI or LO-PASS data. If the data is LO-PASS data, the third digit is then analyzed in block 503 to determine if the data is indicative of the scan entering or leaving a flaw. The entering LO-PASS data is then analyzed in block 504 to determine if it is the last data byte of the scan line. If it is, then it is top of board data and is stored in Buffer X as indicated by block 505 and the pointer is indexed to the next location in the flaw data buffer is indicated by block 517. If the LO-PASS data is not the last byte, then it is stored in Buffer A as indicated by block 506 and the pointer is indexed to the next location. If the LO-PASS data byte is not indicative of the scan line entering a flaw, then the data byte is indicative of the scan line leaving a flaw and is stored in Buffer B as indicated by block 507 and the pointer indexed to the next location.

If the data byte is HI-PASS data, the third digit is similarly analyzed in block 508 to determine if the byte data is indicative of the scan line entering or leaving a flaw. If the data is indicative of the scan entering a flaw, then it is stored in Buffer C as indicated by block 509 and the pointer indexed to the next location. Likewise, if the data is indicative of the scan line leaving a flaw, it is stored in Buffer D as indicated by block 510 and the pointer indexed to the next location.

Returning to block 501, if the data byte is not an X byte, then it is a Y byte. The Y bytes are first analyzed in block 511 to determine if the second bit is a logic one (1) indicative of the presence of HI-PASS data or the special End of Frame byte or is a logic zero indicative of either the special End of Board byte or simply the absence of HI-PASS data. If a logic one is present the data byte is next analyzed in block 512 to determine if it is the special End of Frame (EOF) byte. If it is, the program for forming location of occurrence buffers is exited then proceeds to forming and enlarging the rectangles. If the byte is not the End of Frame Byte, the location of the data is stored in Buffer F, as indicated by block 513 and the pointer indexed to the next location.

If the second bit of the Y byte is a logic zero (0), the byte is analyzed in block 514 to first determine if it is the special End of Board (EOB) byte. If it is, the program is exited. If the Y data is not the End of Board byte, the third bit is then analyzed in block 515 to determine if LO-PASS data was generated during the particular scan. If LO-PASS data was generated, the location of Y byte is stored in Buffer E as indicated by block 516 and the pointer is indexed to the next location. If the byte does not contain LO-PASS data, the pointer is indexed to the next location in the data buffer, the same as if data had been stored in one of the buffers.

The data is stored in each individual buffer according to its location of occurrence with each buffer storing a different type of occurrence, i.e., HI-PASS X byte entering, HI-PASS X byte leaving, etc.

The data stored in each buffer forms a histogram indicative of the number of the particular type of occurrence that occurred at the particular location. Each histogram represents a flaw, and comprises a group of sequential storage locations in each buffer. The number of histograms in each buffer is indicative of the number of flaws present on the board within a given scan frame. The buffers A, B, C, D, E, F and X and their counterparts from the opposite side of the board comprise the Location of Occurrence Buffers, block 410 of FIG. 12.

The program logic for forming the rectangles about each flaw indicated by block 412 on FIG. 12 is shown in the flow diagrams of FIGS. 19A through 19D. These diagrams are limited to the formation of the rectangles from the LO-PASS data and receives information from the location of occurrence buffers A, B, and E created in FIG. 18. The flow diagrams for forming rectangles about HI-PASS data from buffers C, D and F are similar and therefore are not shown.

Referring first to FIG. 19A, the program for forming rectangles about each flaw is entered and the pointers initialized as indicated to the LO-PASS entering data stored in buffer A. The data is serially extracted from buffer A and is compared in block 518 with a threshold value (predetermined number of occurrences) to remove any extraneous signals which may be considered as noise. Normally, four or five occurrences at a given location are indicative that a flaw is present. If the number of occurrences is less than the threshold value, the data is discarded as noise and the analysis is indexed as shown in block 519 to the next location in buffer A. If the number of occurrences is greater than the threshold value, it is then analyzed in block 520 to determine if the data received is the first occurrence. If it is the first occurrence, the location of the first occurrence data which exceeded the threshold is stored in a buffer G as shown in block 521. If the data received is not first occurrence data, then the analysis is indexed to the next location in buffer A. Buffer G only stores the location of the first occurrence of data from each histogram (flaw) stored in buffer A having a value above the threshold.

The program then proceeds to analyze the data in buffer B. The pointers are initialized and the LO-PASS leaving data stored in buffer B is extracted then compared in block 522 with a predetermined threshold value. If the number of occurrences is not greater than the threshold, the analysis is indexed as shown in block 523 to the next location in buffer B. If it is greater, its location is temporarily stored as indicated by block 524 until it is replaced by a subsequent occurrence having a value greater than the threshold. The location stored in the temporary storage is always the location of the last occurrence in buffer B for each flaw having a value greater than the threshold. The data is then analyzed as shown by block 525 to determine if the location being analyzed is the last data location for each histogram stored in buffer B having a value greater than the threshold value. If it is, the location in the temporary storage is placed in buffer H as indicated by block 526, otherwise the analysis is indexed to the next location.

Figures 19B, 19C:
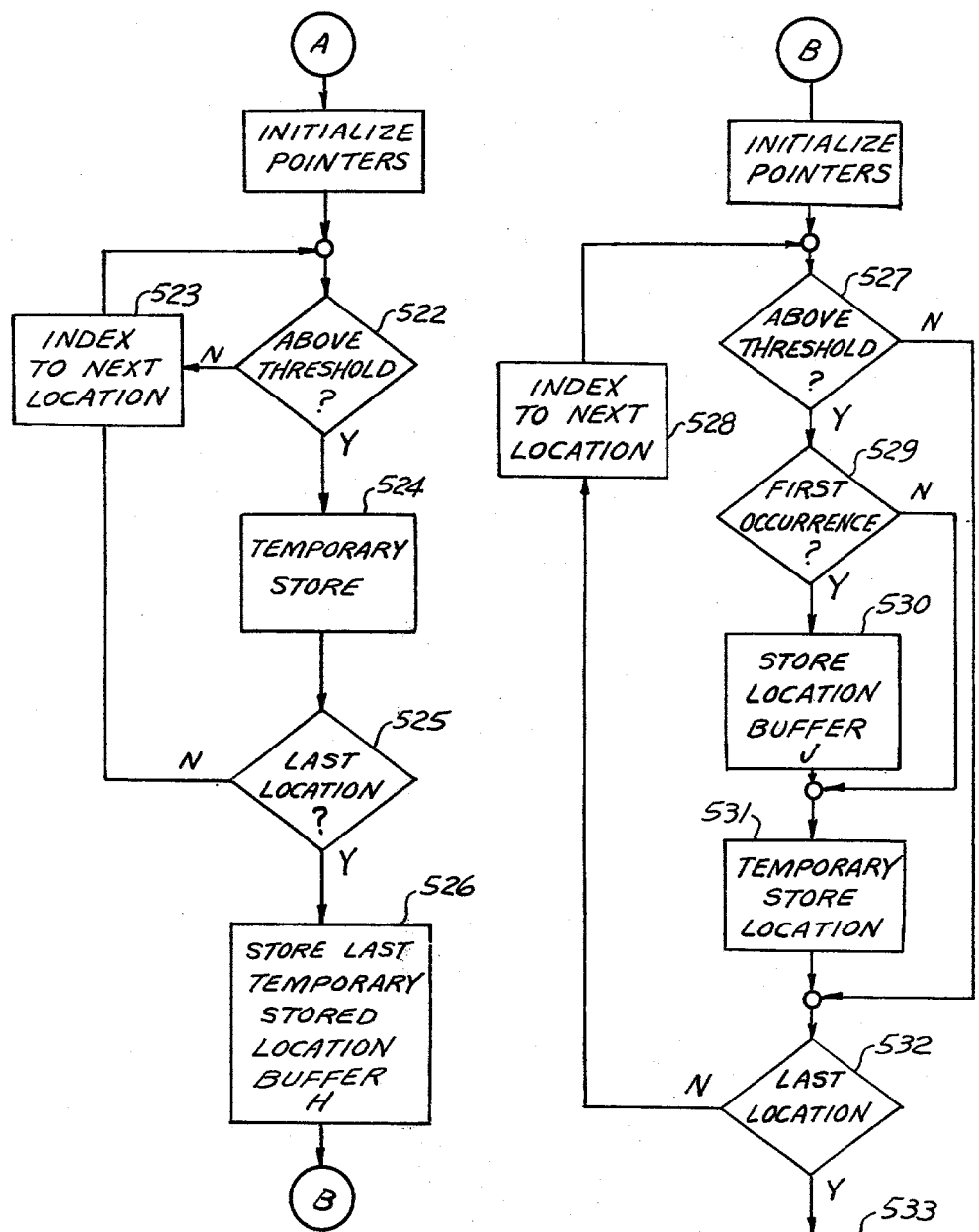

Referring now to FIG. 19C, the program proceeds to analyze the LO-PASS Y data stored in location of occurrence buffer E. The pointer is initialized and the LO-PASS Y data is extracted then compared to a threshold value as indicated by block 527 to determine if the number of occurrences in a given location are greater than the threshold value. If the data from the location of occurrence buffer E is not above the threshold value, the analysis proceeds to determine if the data is from the last location in buffer E as indicated by block 532. If it is not, the analysis is indexed to the next location in buffer E as indicated by block 528. The data which is above the threshold is then analyzed as indicated by block 529 to determine if it is first occurrence data. If it is first occurrence data, its location is stored in buffer J as shown by block 530 and temporarily stored as indicated by block 531. If it is not the first occurrence, then its location is temporarily stored as indicated by block 531 in the same manner as the locations from buffer B are temporarily stored. The program then queries block 532 if the location being analyzed is the last location. If it is, the location stored in the temporary storage 531 is placed in buffer I as shown in block 533. If it is not, the analysis is indexed to the next location in buffer E. This process is repeated until the locations of the first and last occurrence data from each histogram is stored in buffers I and J respectively. At the end of this process, the data stored in buffers G, H, I and J are indicative of the boundaries of rectangles formed immediately about each flaw.

The program then proceeds to generate a top of board (TOB) buffer from the data in buffer X. The details of the process for forming the Top of Board buffer are shown on FIG. 19D. In the forming of the Top of Board buffer, the data in buffer X is examined twice, first to determine the maximum and minimum height of the board in each frame then to find, if any exists, any area within the frame which is well below the maximum height which would be indicative of a hole such as would be caused by cutting through a loose knot appearing at the top of the board.

Referring to FIG. 19D, the data in buffer X is individually analyzed as indicated by block 810 to determine if examination to be performed is the first or second examination as indicated above. If the examination is the first examination of buffer X, the data extracted from buffer X is then examined to determine if its value is larger than the largest value of X data stored in the Mx buffer. If it is, the larger value is stored in the Mx buffer as indicated by block 814 and the smaller value discarded. If it is not, the process continues as indicated by block 618 to determine if the value of the extracted data is less than the current value stored in the Mn buffer. If the value of the data is less than the current value stored in the Mn buffer, the new lower value is stored in the Mn buffer as indicated by block 818. The process then determines as indicated by block 820 if the extracted data is from the last location in buffer X. If it is not, the process is indexed to the next location in buffer X as indicated by block 822. If it is the last location, the final values stored in the Mx and Mn buffers are stored in the Top of Board (TOB) buffer as indicated by block 824. The first value extracted in the first examination is placed in both the Mn and Mx buffers as the initial reference, thereafter the values stored in the Mx and Mn buffers are a result of the decisions indicated by blocks 812 and 816.

After the data in the Mx and Mn buffers are stored in the TOB buffer, the pointer is reset to the first location in buffer X as indicated by block 826 and a flag set indicating the second examination of the data in buffer X. The analysis performed by block 810 is now negative and the analysis of the data proceeds to determine if the data stored in buffer X is less than the maximum board height Mx stored in the TOB buffer minus a predetermined value "C" as indicated by block 828. If it is not, the data is analyzed to determine if the data was extracted from the last location in buffer X as indicated by block 836. If it is the last location, the program is exited. If it is not, the analysis is indexed to the next location in buffer X as indicated by block 822.

If the value of the extracted data is less than Mx-C), the data is next examined to determine if the data having a value less than (Mx-C) is a first occurrence as indicated by block 830. If the data is a first occurrence, it is stored in the TOB-Left buffer as indicated by block 832. If the data is not a first occurrence, it is temporarily stored in the TOB-Right buffer as indicated by block 834. The data stored in the TOB-Right buffer is replaced by any subsequent data having a value less than Mx-C so that the last data stored in the TOB Right buffer represents the data which defines the right hand edge of data having a value less than Mx-C. The process then proceeds to inquire if the data analyzed had been extracted from the last location in buffer X. If it is not, the process indexes to the next location in buffer X and the analysis is repeated. If the data was from the last location, the process is exited as indicated by block 836 and the program proceeds to form enlarged rectangles about the flaws. The TOB buffer, TOB-Left and TOB-Right buffers define the maximum and minimum height of the board in each frame, the beginning or left edge and the end or right edge of any defect present if there is one. This defect will subsequently be treated as a flaw during subsequent operations.

Figure 20:
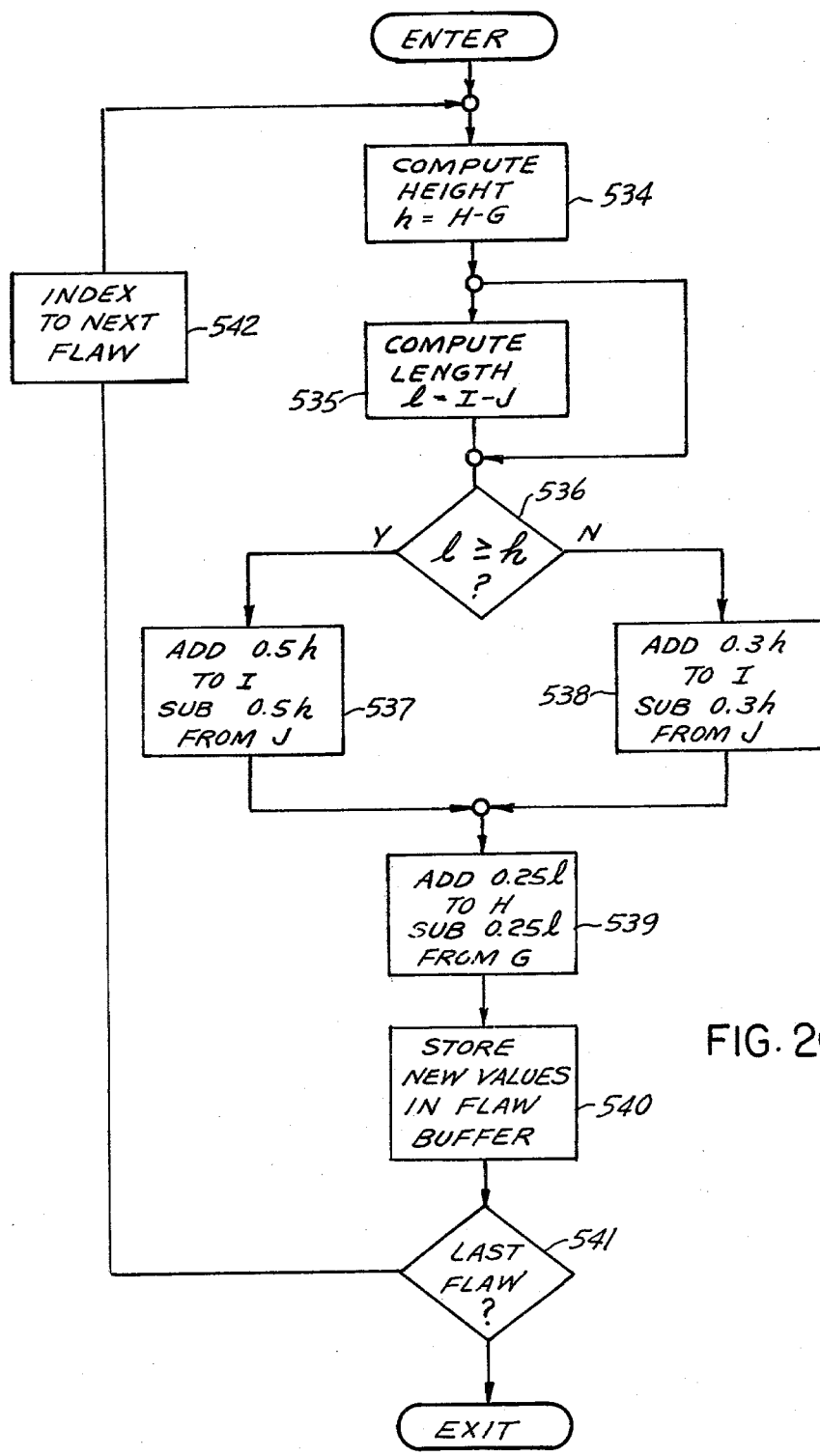
FIG. 20 is a flow diagram illustrating the program logic for forming enlarged rectangles about each flaw.

The flow diagram for computing the enlarged rectangles about the flaw indicated by block 412 of FIG. 12 is shown in FIG. 20. The height of each rectangle is computed from the data stored in buffers G and H by subtracting the location of the first occurrence data in buffer G from the location of the last occurrence data in buffer H as indicated by block 534. Likewise, the length of the rectangle about the flaw is computed from the data stored in buffers I and J as indicated by block 535. The length and the height of the rectangle are then compared to determine if the length is equal to or greater than the height or the height is greater than the length as shown in block 536. If the length is equal to or greater than the height, the length is then enlarged by adding a first predetermined distance to the location of the data contained in buffer I and subtracting this same distance from the location of the data contained in buffer J. The first predetermined distance may be a fixed distance or a function of either the length or height of the flaw as indicated by block 537. If the length is less than the height, the length is then enlarged by adding a second predetermined distance to the location of the data contained in buffer I and the same distance subtracted from the location data stored in buffer J. The second predetermined distance may also be a fixed distance or a function of either the length or height of the flaw as shown in block 538. The height of the rectangle is then enlarged by adding a third predetermined distance to the location of the data contained in buffer H and subtracting the same distance from the location of the data contained in buffer G as shown in block 539. The new locations of the enlarged flaw boundaries are placed in the flaw buffer as indicated by block 540. The process then inquires, as indicated by block 541, whether or not the flaw was the last flaw in buffers G, H, I, and J. If it is not, the process indexes each buffer to the next flaw as indicated by block 542 and the enlargement process is repeated for the next flaw. If it is the last flaw, the process is exited as shown. A similar flaw enlargement process is also performed with the data stored in the buffers storing the edge locations of the other flaws stored in other buffers as previously indicated.

Figure 21:
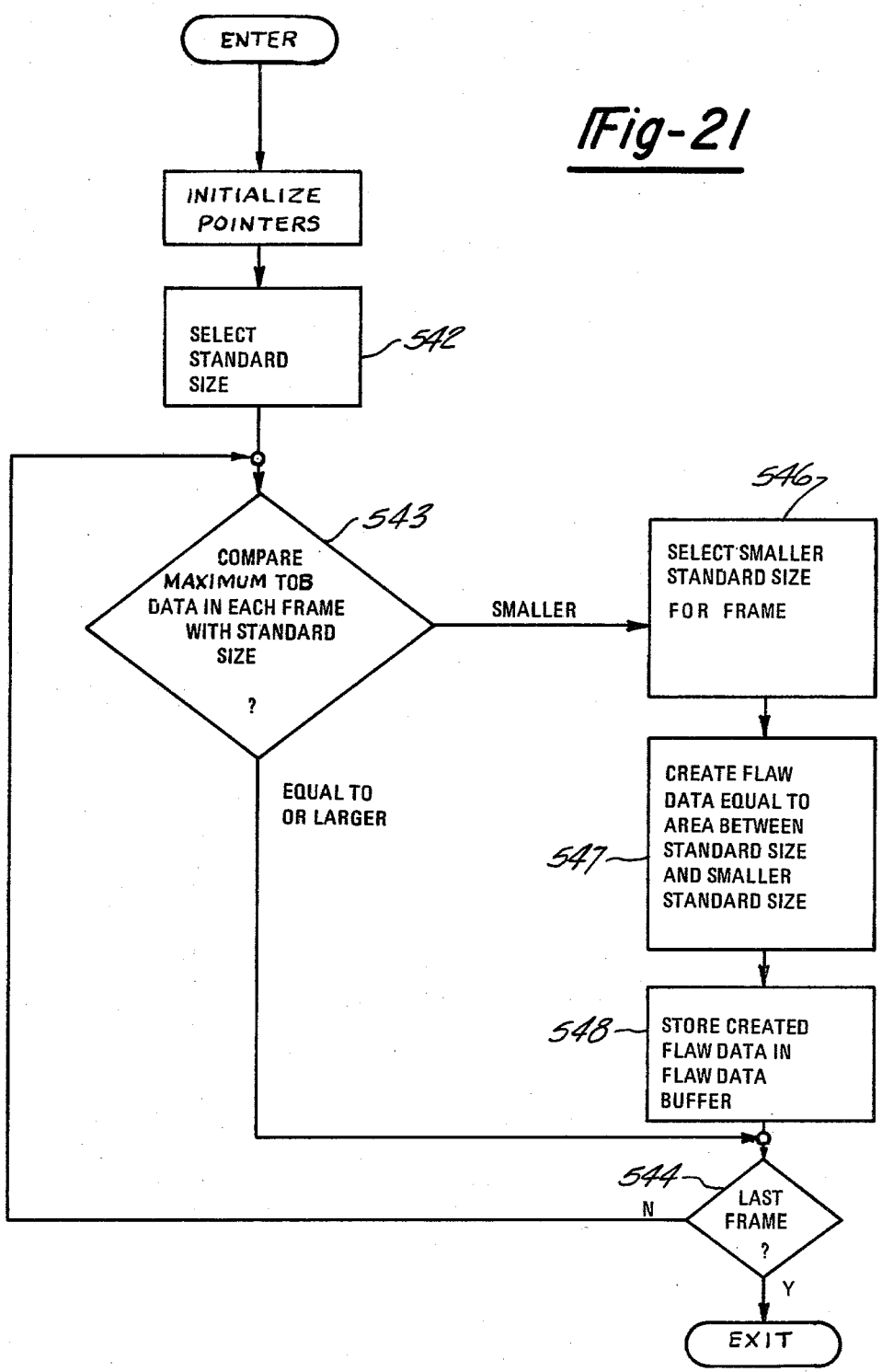
FIG. 21 is a flow diagram illustrating the search for narrow lumber.

The flow diagram for the search for narrow lumber indicated by block 418 of FIG. 12 is illustrated in FIG. 21. The data for forming a table containing the maximum and minimum heights of the board for each frame is obtained from the Top of Board buffer described with reference to FIG. 19D. The maximum height of the board in each frame is compared as indicated by block 542 with a table of standard sizes which comprises the sizes entered into the computer in the form of data entry. The standard sizes are indicative of the heights of the various products to be cut from the board. The standard size selected is the largest standard size which is smaller than the maximum board height determined from the table. The maximum height of the board for each frame is then compared as indicated by block 543 with the selected standard height to determine if maximum minimum height of the board within that frame is smaller or larger than the standard height. If the maximum height of the board within the frame is equal to or larger than the standard height, the data is analyzed in block 544 to determine if the maximum top of board data just analyzed is for the last frame or not. If it is not from the last frame, then the comparator is indexed to analyze the maximum top of board data for the next sequential frame. If the data is for the last frame, this routine is then exited as indicated and the process proceeds to eliminate flaw overlap as indicated by block 420 of FIG. 12. If the maximum height of the board in any given frame is determined to be smaller than the standard size, a new search comparable to that performed in block 542 is made to select a smaller standard size for that frame as indicated by block 546. For that particular frame then, flaw data is created which is equal in area between the first selected standard size and the smaller standard size and has a width equal to the width of the frame as shown by block 547. This created flaw data is then stored in the flaw buffer as indicated by block 548 of FIG. 21. Again the process inquires, as indicated by block 544, if the data just analyzed was for the last frame or not, and proceeds as previously described.

Figure 22:
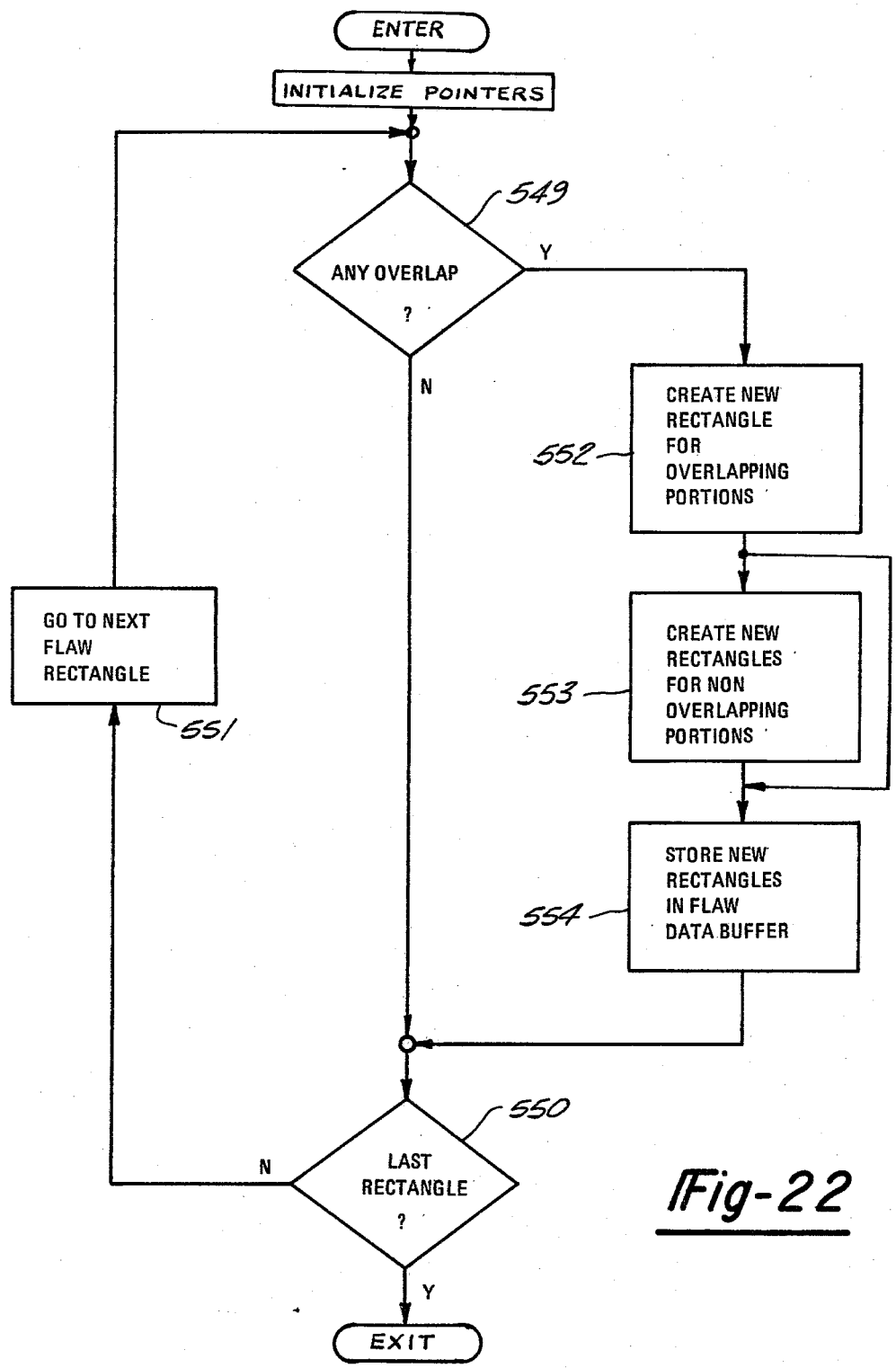
FIG. 22 is a flow diagram illustrating the elimination of the overlap of the enlarged rectangles.
Figure 23:
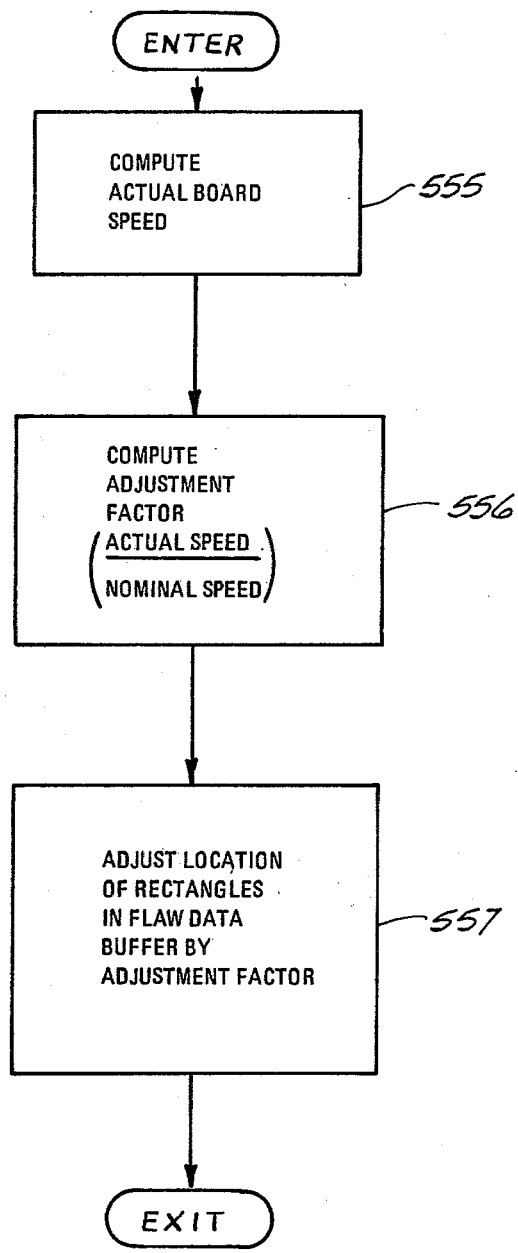
FIG. 23 is a flow diagram illustrating the board speed adjustment process.

The elimination of flaw overlap indicated by block 420 of FIG. 12 is illustrated in the flow diagram of FIG. 22. The elimination of flaw overlap procedure is entered and the pointers initialized as shown. The enlarged rectangles about the flaws stored in the flaw data buffer are sequentially analyzed with respect to adjacent rectangles to determine if there is any overlap between the enlarged rectangles as indicated by block 549. If there is no overlap with an adjacent enlarged rectangle, the data is then analyzed block 550 to determine if this is the last rectangle stored in the flaw data buffer. If it is not, the analysis to determine overlap is indexed to the next flaw rectangle as indicated by block 551. If an overlap of the enlarged rectangle is detected, then a new rectangle for the overlapping portions of the two flaws is created as illustrated in block 552 and the locations of the boundaries of the new rectangle are stored in the flaw data buffer as indicated by block 554. New rectangles are also created as shown in block 553 for the non-overlapping portions of the enlarged rectangles and the locations of the boundaries for the new rectangles are also stored in the flaw data buffer.

The location of the flaws stored in the flaw data buffer is based on the board passing through the scanner at a nominal speed. However, the speed of the board passing through the scanner may differ from this nominal speed. Therefore, the position or the location of the flaw boundaries must be corrected for the difference between the actual speed and the nominal speed of the board as it passes through the scanner. The portion of the computer program that performs this function is shown in the flow diagram in FIG. 23. The actual board speed is computed from data received from sensors measuring the actual board speed as indicated in block 555. A correction factor is then computed by dividing the actual speed by the nominal speed as illustrated in block 556. The correction factor may also contain the conversion factor for units of measure. The location of all the flaw data in flaw data buffer is then adjusted in the Y direction by multiplying this data by the adjustment factor as shown by block 557.

The details of the optimization technique for product selection, and board cutting encompassing the functions of blocks 424, through 430 of FIG. 12 are shown on FIGS. 24 through 40.

The input information required for the selection and lumber cutting program comprises product order entry list and the data in the Flaw Data Buffer. The product order entry list facilitates the search for pieces having the highest designated priority or value and which contain numerical descriptors of the pieces to be processed. Flaw data buffer contains the location, quality and quantity of every flaw for each board. The search for those pieces of lumber resulting in an optimum yield (i.e. satisfying the product order list) begins by attempting to obtain the most desirable product pieces as specified within the product order list.

Upon determining which product pieces can be taken from a board, the program outputs a set of dimensions designating a series of locations where the board is to be cross-cut or marked. The intelligence regarding the type and quantity of each product taken can be used to update a cumulative table yielding an inventory of each product cut. This inventory can be used to re-prioritize the priority list as required.

Prior to describing the specific computer program and the following flow diagrams, a diagrammatical illustration of the product search and board cutting process is presented. A typical sequence of events leading to the extraction of a qualified product from a board, having a number of randomly spaced flaws, is pictorially illustrated in FIG. 24. There is shown a board 10 of length L, that has been processed through the electrooptical scanner and the location of the flaws determined. The first step is to identify segments ($s_i$) of "good wood". Good wood is defined as some length of wood that does not contain any unconditionally non-acceptable flaws. The location of the first segment ($s_1$) is designated by an entrance coordinate $y_1(s_1)$ and exit coordinate $y_2(s_1)$ which are the locations of the right edge and the left edge of two successive non-allowable flaws respectively. Each segment of good wood is found from an analysis of the data in the board's flaw buffer. The next step is the selection of a qualified product ($P_p$) from the segment of good wood, such as product ($P_1$). Remainder segments (r) are usually generated whenever a selected product ($P_p$) is smaller than segment (s). Subsequent processing cycles attempt to extract additional products from each remainder segment. The positions of cut-marks ($y_c$) necessary to yield the desired products are generated, sorted and stored in a cut-mark buffer. They are then sent to an Output Device 22 such as a saw to cross-cut the board at the designated ($y_c$) cut-marks.

The processing of each board (k), segment (s) and remainder (r) will continue until it is not possible to obtain any product that conforms to the product contained in the ordered entry list. The non-conforming pieces are routed for secondary usage.

Figure 24:
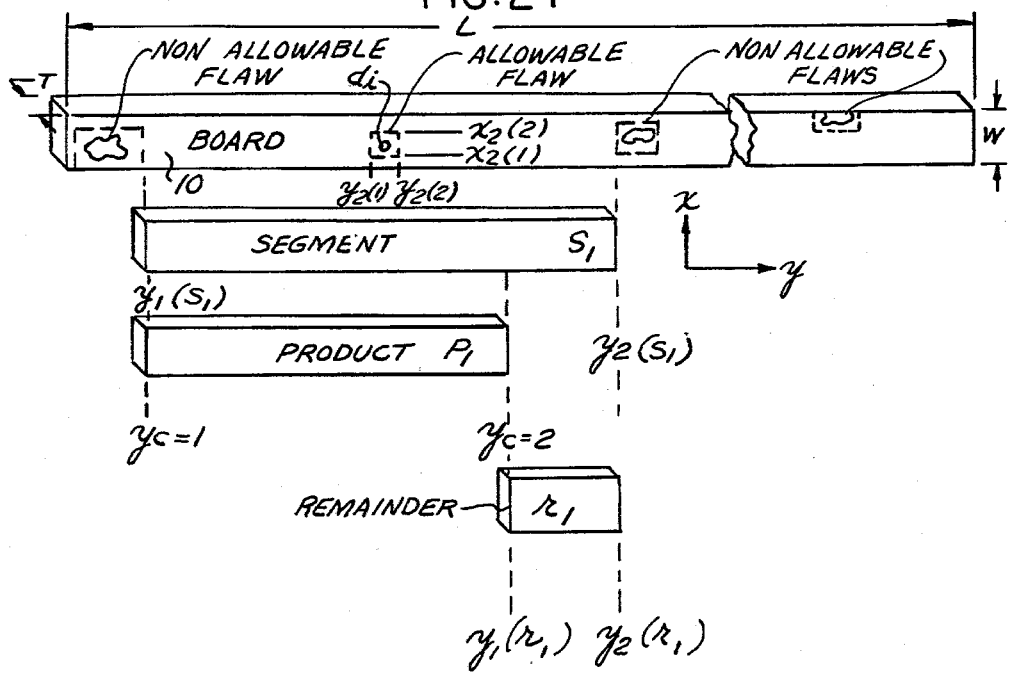
FIG. 24 shows a typical board and its subdivisions according to program breakdown.
Figure 25:
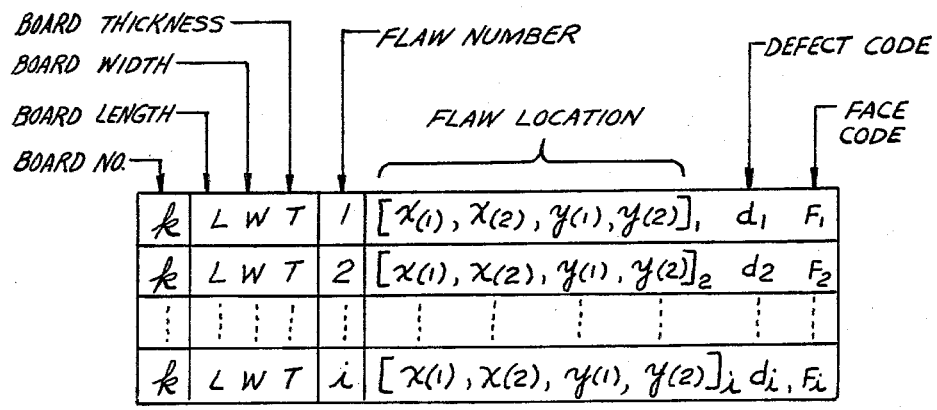
FIG. 25 shows the flaw data format as stored in flaw data buffer.

To enhance board processing, the data contained within the flaw data buffer is restructured for use by an Optimizing, Selection and Cutting algorithm. The input data set can be classified into a Reference data set including such variables as board number (k), length (L), width (W) and perhaps board thickness (T) and an Item data set having a board flaw index (i), information defining the locations of the enlarged rectangles framing the $i^{th}$ flaw on the board (k), a flaw defect category $D_i$ numerically designating the quality or type of each flaw and a face index F, where F=1, 2 or 3 indicates the facial location or side of occurrence of each flaw, that is, a flaw on the board's front face (F=1), back face (F=2) or a flaw that extends through to both faces (F=3). The flaw buffer data designating the location of each enlarged rectangle consists of information defining the location of the four edges of each rectangle in board coordinates. FIG. 25 illustrates the data format of the restructured flaw data buffer and FIG. 24 diagrammatically illustrates the physical significance of the data. The parameters $x_i(1)$ and $x_i(2)$ are the lower and upper flaw boundaries measured across the width of the $i^{th}$ flaw and where $y_i(1)$ and $y_i(2)$ are the entry and exit boundaries of the $i^{th}$ flaw along the Y coordinate axis.

The second input data set required for the optimization program is the product order list.

The format of a typical product order list is shown in FIG. 26. The list is a ranked classification of the products, $P_p$, that is, the product having the lowest number, i.e., p=1 is the most desirable product. The product order list comprises specification data including such information as: product index p, the maximum $1_{T2}$ and minimum $1_{T1}$ length of a product. In addition, the product list contains codes to designate face or rip grade products, and finally, a numerical index code to indicate which of the many types of flaws ($D_j$) existing in the uncut board are permitted in the product.

In addition to the data storage buffers required to store the input data, the selection and cutting algorithm utilizes a number of additional storage buffers, in particular, a segment, a remainder, a cut-mark and a yield data buffer. The end locations of each segment (s) of the $k^{th}$ board are stored in a segment buffer. The format of data to be placed in the segment buffer is shown in FIG. 27(a), where $Y_1(s)$ and $y_2(s)$ are the entry and exit locations of each section of good wood in absolute board coordinates.

Secondary information, generated during segment processing, concerning the entrance and exit locations of each remainder piece (r) is stored in the remainder buffer. The format of the remainder data is illustrated in FIG. 27(b) where $y_1(r)$ and $y_2(r)$ correspond to the entry and exit locations of the $r^{th}$ remainder of the $k^{th}$ board.

An output of the computer program is the designation of the locations of a series of cut-marks $y_c$, describing where each board is to be cut. These cut-marks are stored in the cut-mark buffer in the format shown in FIG. 27(c). As each board is analyzed, the total number of pieces cut against the list (n), and the total number of pieces cut to the $p^{th}$ product ($n_p$) are generated and stored in the yield buffer in the format shown in FIG. 27(d).

The lumber cutting program is structured in a series of computational modules or procedures. The computational flow proceeds in a "top down" manner, that is, the program code is arranged to perform processing functions in layers of increasing detail.

Figure 28:
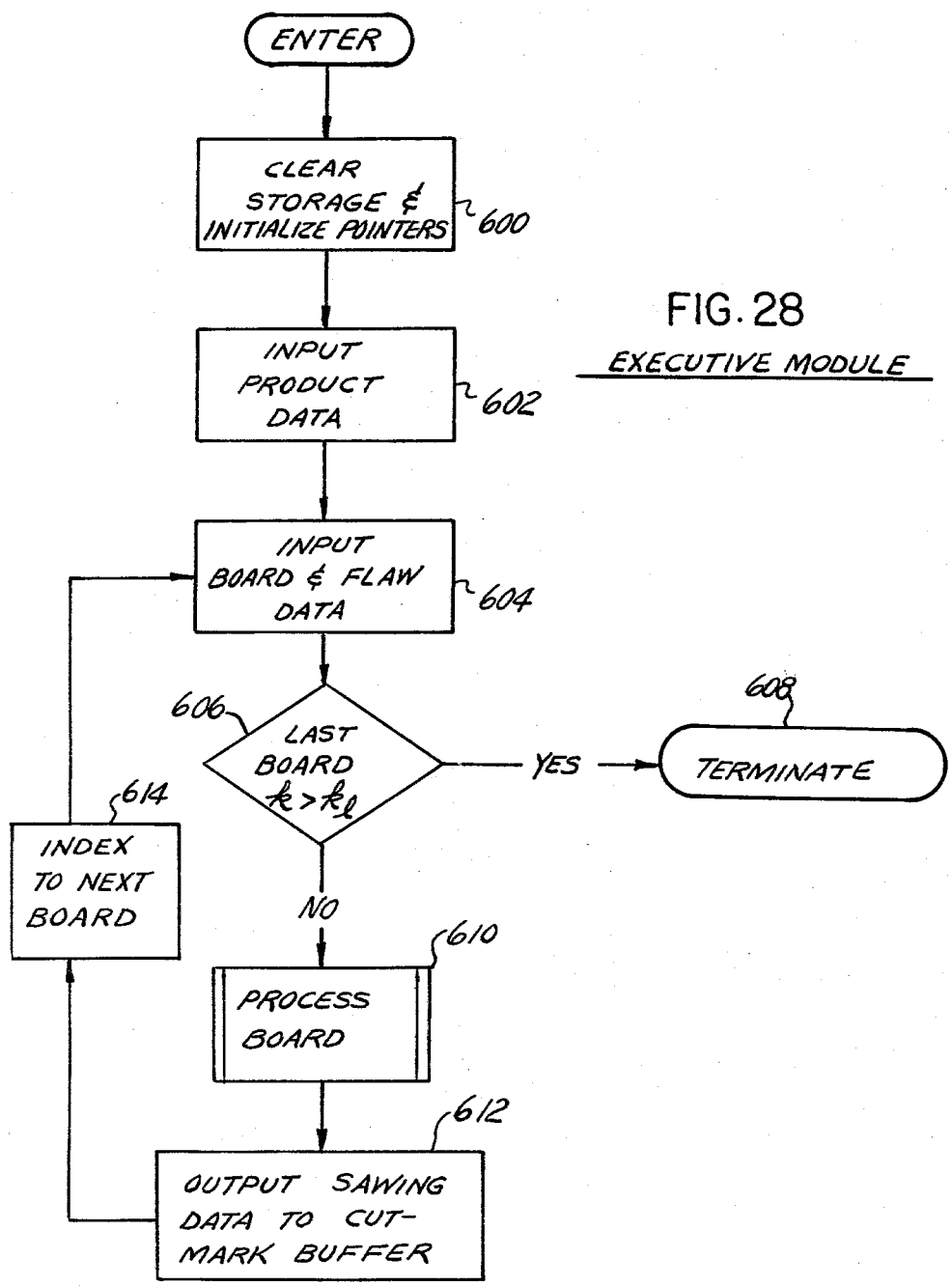
FIG. 28 is a program flow chart of the program general algorithm.

FIG. 28 is a flow diagram of the Executive Module of the cutting algorithm. All data storage buffers and registers are cleared and the pointers initialized as indicated by block 600. Product data is obtained from the order entry buffer, as shown by block 604. Flaw and board data are obtained from the flaw data buffer as indicated by block 604. The number of the board being processed is compared as indicated by block 606 to an index number $k_1$ designating the last board. If the board number k indicates that the last board has been processed, the program is terminated as indicated by block 608. If not, the $k^{th}$ board is processed as indicated by block 612 resulting in 1.) the outputting of saw-cut data to the cut-mark buffer 614, 2.) product yield count, and 3.) indexing the board number.

After the cut-mark data is output to cut-mark buffer as indicated by block 612, the program is indexed to the next, k+1 board as indicated by block 614.

Figure 29:
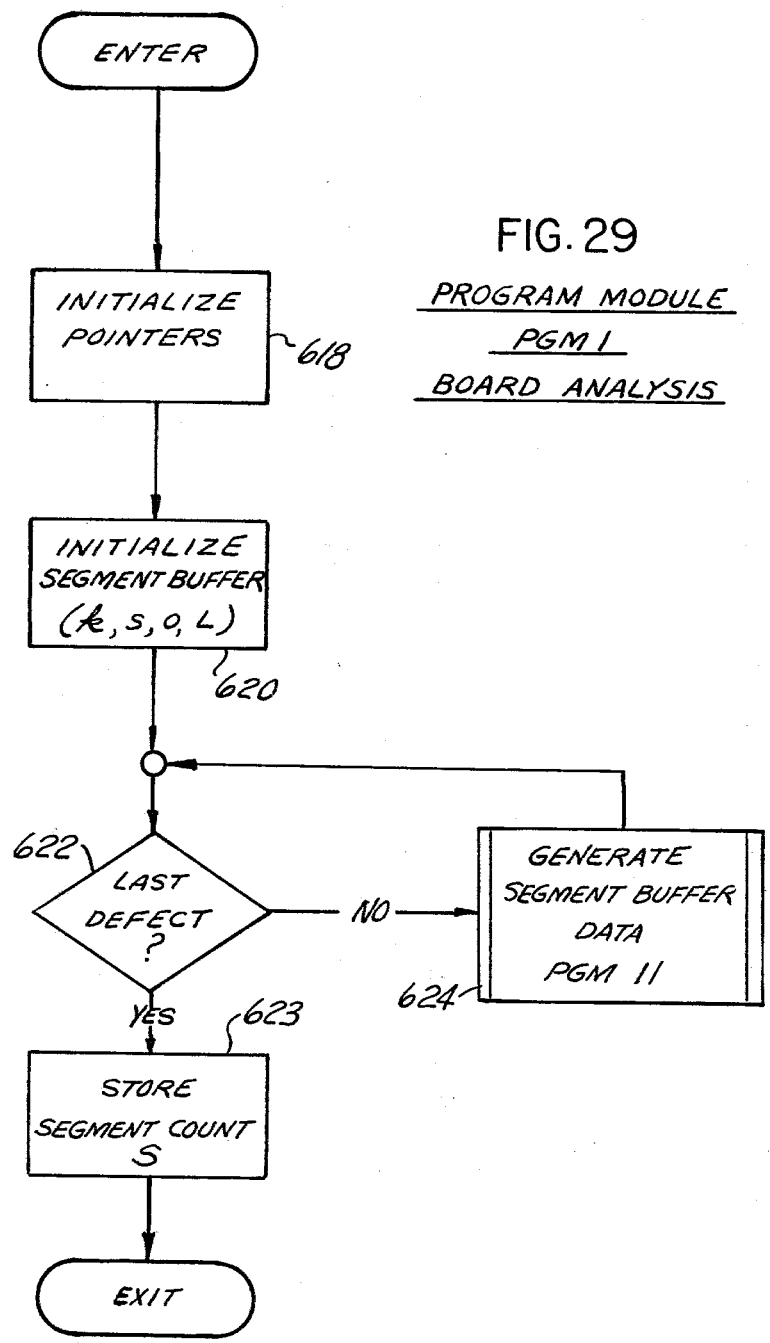
FIG. 29 is a flow diagram for program module PGM1.
Figure 30:
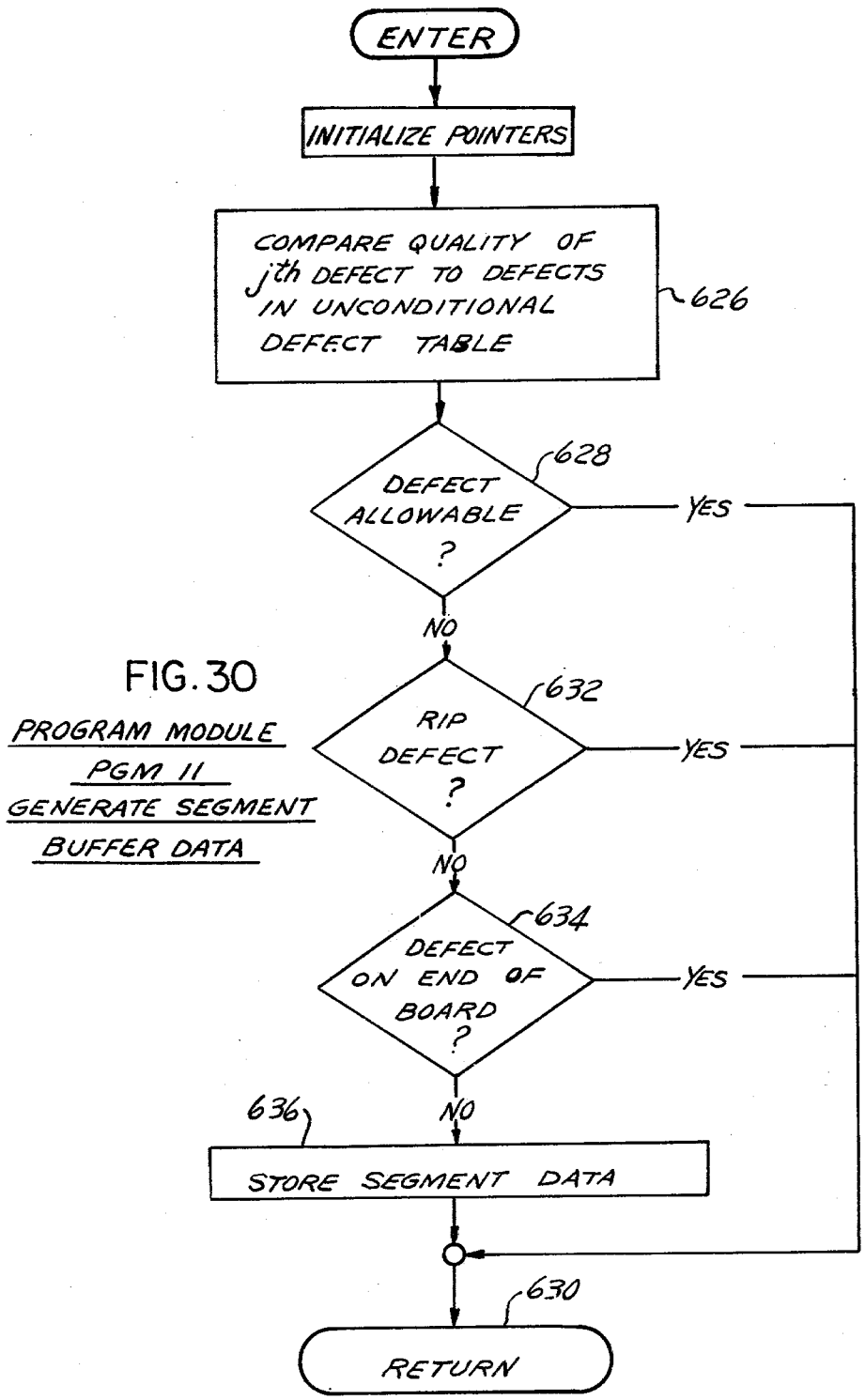
FIG. 30 is a flow diagram for program module PGM11.

The processing of the $k^{th}$ board, block 610, begins by entering program module PGM1 as shown on FIG. 29. This program module generates the data for the segment buffer by eliminating those portions of the board having flaws which are not allowed on any product. The elimination of these not allowed flaws results in the segmentation of the board as shown in FIG. 24.

The PGM1 program module initializes a variety of pointers or indices 618 such as the Remainder index (r), the Defect index i, the Segment index s, and the Cut-Mark index c. The data in the segment buffer is initialized 620 to reflect the board number k, and the initial segment number s=1. During the initial pass-through of this program module, the entire board is considered as a single segment, consequently the beginning $y_1$ and ending $Y_2$ dimensions of this first segment are set to 0.0 and a number indicative of the board length L, respectively, as shown in block 620. A decision is made to determine whether or not the last flaw on a particular board has been analyzed as indicated by block 622. This is done by comparing the defect index i to the number indicative of the highest flaw number on the $k^{th}$ board. If the last defect of a board has been analyzed, the program stores a segment count 's' in the segment buffer as indicated by block 623. If the last defect on the board has not been processed, the program module PGM1 continues to examine the entire length of $k^{th}$ board generating segment buffer data for each additional segments of good wood as indicated by block 624. The details of the generation of segment buffer data proceeds with the flow chart of program module PGM11 is shown on FIG. 30.

Certain types of flaws such as those which impair the strength of a piece of lumber, e.g., large cracks or loose knots, are not permitted in any product. In essence, they are defects that are non-allowable.

To determine whether or not a defect is non-allowable requires comparing the quality of the $i^{th}$ defect contained within flaw data buffer of FIG. 25 with the list of allowable defects contained within the product order entry list of FIG. 26 or alternatively with a table containing only the code of non-allowable defects as indicated by block 628. If the defect is allowable, the processing returns to Program Module PGM1 shown on FIG. 28. Given that a non-allowable flaw has been identified, secondary criteria are applied to minimize waste. The flaw may be close to a top or bottom edge, indicating that the wood is of rip grade quality permitting recovery of a significant portion of board width. Thus, a test of the width of the flaw relative to board width is made as indicated by block 632. If a majority of the board's width can be salvaged, the non-allowable area is retained. Otherwise, the defect is categorized as non-allowable and must be removed. Similarly, defects residing near the ends of each board as indicated by block 634 are considered non-allowable and must be removed. Segment data indicative of the end locations between non-allowable flaws is stored in the segment buffer as indicated by block 636. The stored segment data indicates the locations and number (s) of each segment.

To facilitate the understanding of the product searching procedures, there is shown on FIG. 31, an actual board 640 processed by the program having a plurality of defects illustrated as enlarged rectangles 642a, 642b, 642c, 642d and 642e. The cross-hatched rectangles indicate non-allowable defects. The contents of the flaw buffer data for board 640 is presented in the table shown on FIG. 32 while the content of order entry buffer is as shown on FIG. 26. As can be seen from the flaw data buffer table, FIG. 32, the enlarged rectangles of flaws 642a, 642b and 642e, corresponding to flaws i=1, 2 and 5 span the full width, W, of the board (4.9 inches), and in addition, each flaw extends through to both faces (F=3). These flaws are non-allowable and will cause program module PGM11 to divide the board 640 into three segments 644, 646, and 648 of "good wood" as indicated. The defect i=3 (624c) is less than 50% of the board width and is temporarily permitted to remain in the "good wood" segment 646. Flaw i=4 642d is a permissible flaw residing only on the front face of segment 646. Returning now to FIG. 30, segment data consisting of the entry $y_1(s)$ and exit $y_2(s)$ of each segment is stored in ascending Y coordinate numerical order in the segment data buffer as indicated by block 636.

Segment processing continues upon entering the EXEC1 program module shown in FIG. 33. EXEC1 module controls the search and selection procedure for identifying qualified products from the numerically segmented board. This module maintains pointers or indices to the order entry list, segment storage buffer and remainder storage buffer. Processing continues until all segments and remainder pieces have been tested against every product on the order entry list.

Upon entering Program Module EXEC-1, the physical dimensions of the products, called templates, are sequentially selected from the order entry list in their order of priority as indicated by block 660. The templates are mathematically layed over the segment and the quality of the defects within the area of the segment defined by template are tested against the allowable defects for the product as indicated by block 670. If all the defects are allowable, the portion of the segment lying under the template is tagged as a qualified (Q) product and cut-marks are generated as indicated by block 730. If the defects are not allowable, the portion of the segment is tagged as a remainder.

The program then determines whether or not the same template can be used again as indicated by block 740, that is, can additional products of the same priority be extracted from the good wood left in the segment after the first product has been removed. If it can, the template is moved to the right a full length and the flaw content of the remaining wood underlying the template is again analyzed as indicated by block 670. If the same template does not fit within the length of remaining wood and a remainder exists as indicated by block 750, a template corresponding to next lower priority product p+1 is selected as indicated by block 660 and product extraction proceeds in an identical manner as previously detailed. Processing continues until it is impossible to fit any template (product) to the remaining piece of wood. At this point, there are no usable remainder sections left from the $j^{th}$ segment and the segment index or count (j) is advanced 760 to analyze the next or (j+1) segment of "good wood". If the segment count is less than or equal to the number of segments (s) generated previously in Program Module PGM1 as indicated by block 770, the template pointer is reset to the first template as indicated by block 771 and the processing continues with the new segment (j+1) as previously described. Upon processing the last segment of a particular board, i.e. when "j" is larger than "s", the EXEC1 module ie exited.

Figure 34:
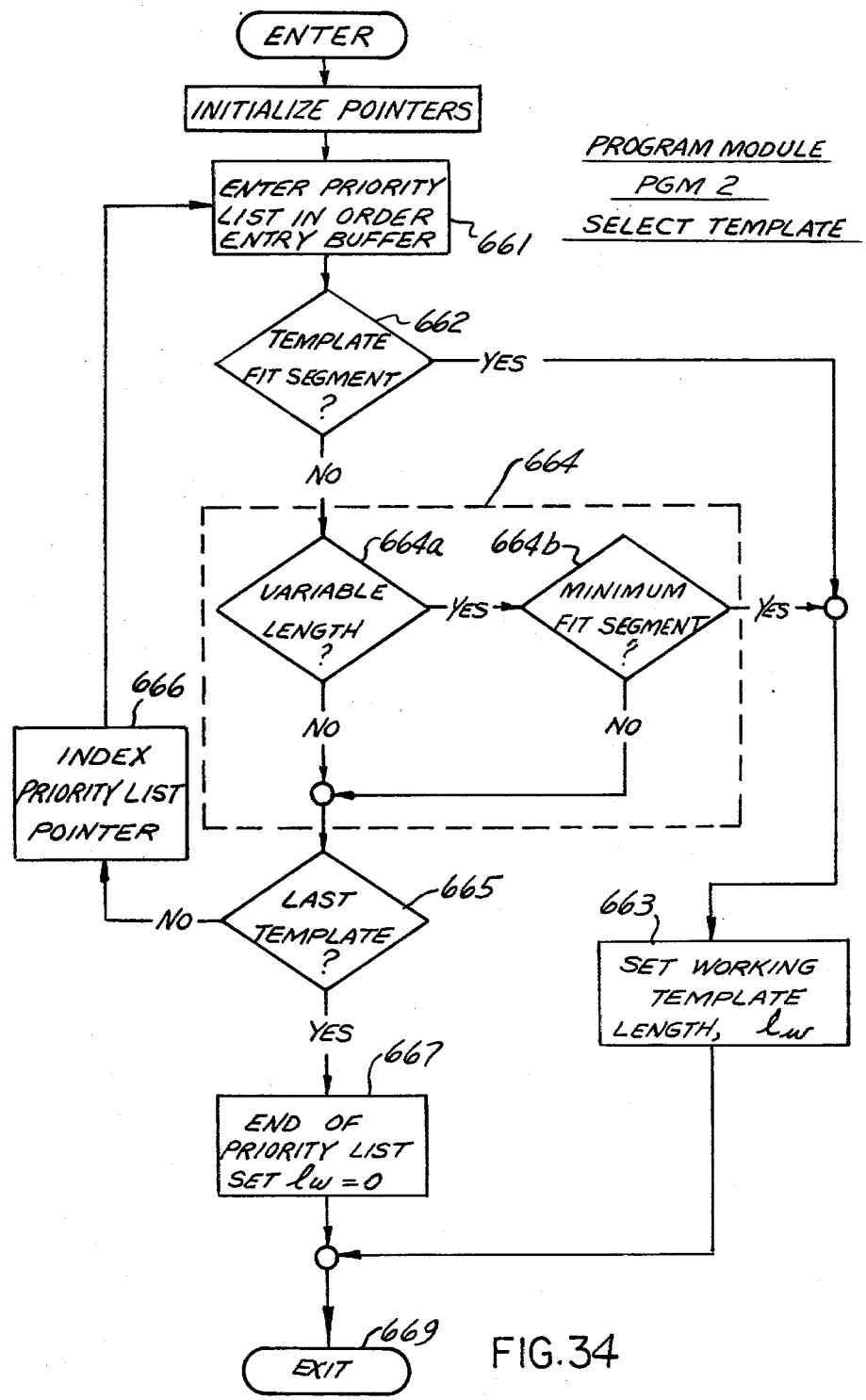
FIG. 34 is a flow diagram for program module PGM2.

The operational flow of the Select Template process indicated by block 660 on FIG. 33, i.e. program module PGM2, is shown on FIG. 34.

The Order Entry List is entered and the highest priority product and its corresponding template selected as shown by block 661. The template for product $P_1$ is mathematically laid over the segment and a determination is made to assure that the template length is not larger than the segment as indicated by block 662. If the determination is affirmative, a template working length, $l_w$, is specified as indicated by block 663 and the program exits to the D-Test (defect test) Program Module PGM3.

The order entry or product list shown by way of example on FIG. 26 is used to analyze the board of FIG. 31. Product $P_1$ has a fixed length of 84 inches, product $P_2$ has a fixed length of 85 inches, product $P_3$ has a fixed length of 31 inches and product $P_{11}$ has a variable length between 9.1 and 18 inches.

Lumber products such as moldings can be fabricated from a number of smaller pieces that can later be joined together. Consequently, product satisfaction can be achieved utilizing pieces of varying length as indicated by product $P_{11}$.

The processing to ascertain whether or not an acceptable product can be taken using a variable length template is performed as indicated in dashed block 664. To determine if a variable length template can be used to satisfy products within the product order list requires scrutinizing the maximum and minimum lengths contained in the product list order entry buffer shown on FIG. 26. If the length of the segment is less than $1_{T2}$, this is indicative of the fact that qualified products may possibly be taken from various segment lengths. The length of the minimum ($1_{T1}$) acceptable length is compared to the length of the segment. If $1_{T1}$ is less than the length of the segment as indicated by block 664b, the working length ($1_w$) of the template is set as indicated by block 663 to be equal to the smaller of the maximum allowable template $1_{T2}$ and the length of the segment thus insuring that the largest length product is taken.

If the selected template, corresponding to the $p^{th}$ priority product, does not fit and it is not the last template as indicated by block 665, i.e., the lowest priority product, the order list pointer is incremented to the next lower priority product as indicated by block 666. If the conformity of the segment to the lowest priority piece or template has been tested and the template still does not fit, it is indicative that end of the list has been reached and the board segment is an unusable remainder and the process is exited as indicated by block 667.

Each candidate product may have certain allowable flaws while other types of flaws are not allowable. Consequently, it is not sufficient to ascertain qualified products by the template selection algorithm of program module PGM2. The program module PGM3 in conjunction with sub-modules PGM31, PGM32, PGM33 and PGM34 examines the length of board lying within the contours of the chosen template to determine the quality of the segments's flaw content and to determine if a qualified product can be extracted therefrom.

Figure 35:
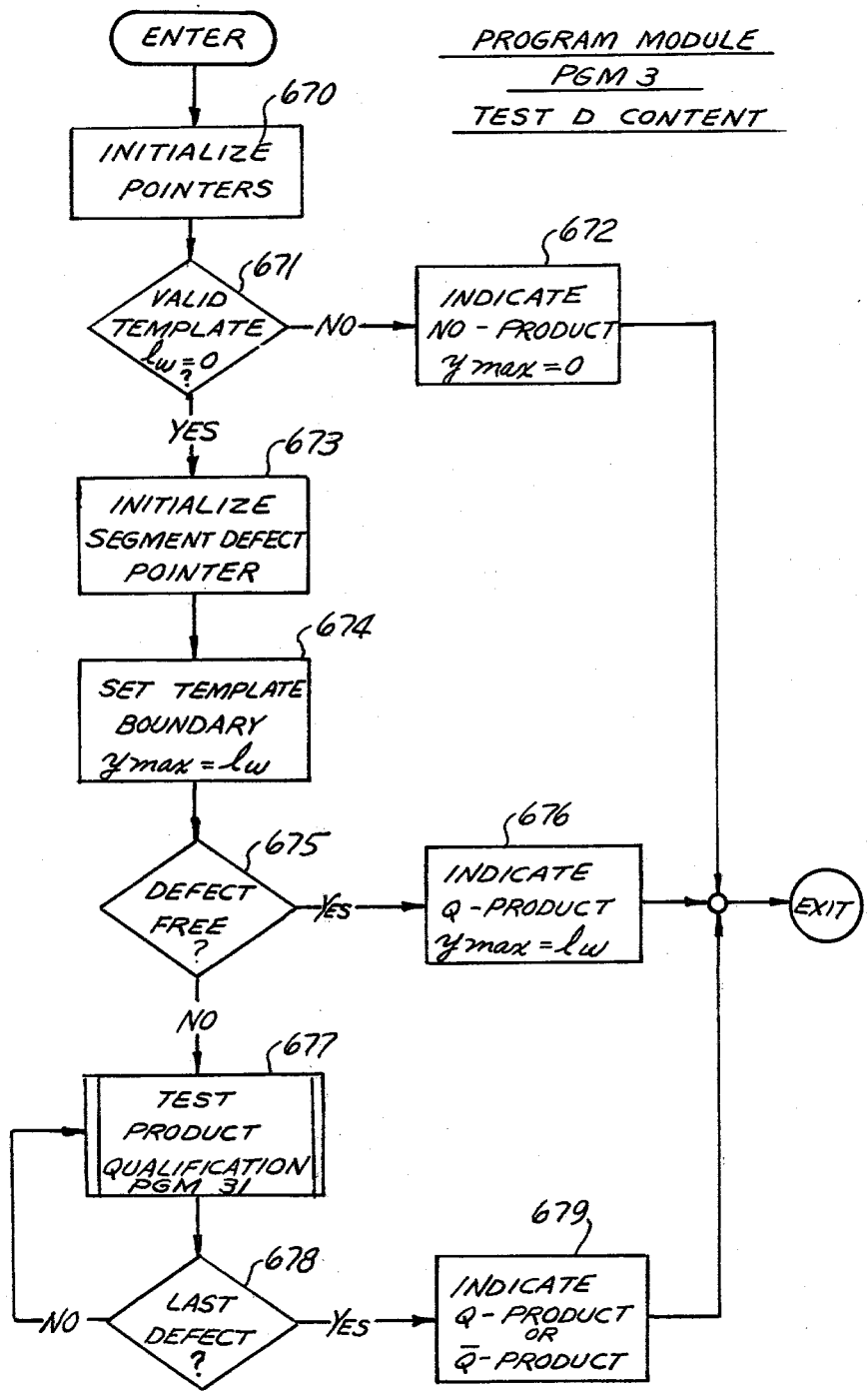
FIG. 35 is a flow diagram for program module PGM3.

The operational flow of the Test D Content block 670 of FIG. 33 is program module PGM3 shown on FIG. 35. Upon exiting the EXEC1 module, FIG. 33, the PGM3 module is entered and the pointers initialized. The parameter $1_w$ previously set in module PGM2 is tested as indicated by block 671. If $1_w$ is zero, an invalid template has been chosen and the variable $y_{max}$ is correspondingly set to zero as indicated by block 672 and exited.

Upon determining that the template is valid, that is, $1_w$ is not zero, the defect index is initialized as indicated by block 673.

The template working boundary or length $1_w$ is initially marked by an acceptance pointer $y_{max}$ at the coordinate corresponding to the right most edge of the template as indicated by block 674. That portion of the board between the template boundaries is examined from left to right to determine the quality of each defect ($d_i$) lying on the board within the template boundaries. If the segment is found to be free of defects as indicated by block 675, the segment under analysis will yield a qualified product as indicated by block 676 corresponding to the size and priority of the selected template. To indicate a qualified product $y_{max}$ will be equal to the board coordinates of the right hand exit boundary of the template. The exit and entry coordinates of the qualified product are stored in a remainder and cut-mark buffer. The template is then shifted to the right such that its left hand edge is coincident to the right hand boundary of the qualified product.

If a defect has been detected in the analysis performed by block 675, then the quality of each defect lying within the segment is sequentially analyzed 677, as indicated by the Test Product Qualification block to assure that such a defect is permitted in the particular product. The Test Product Qualification indicated by block 677 is performed in program module PGM31 shown on FIG. 36.

If it is determined that the wood beneath the template is not a qualified product, i.e., it contains non-allowable flaws, the product is identified as a not qualified ($\overline{Q}$) product as indicated by block 678, and the parameter $y_{max}$ is set to the right-most boundary of the non-allowable flaw $y_1(i)$ in board coordinates.

The PGM3 module is exited with further process control returned to the EXEC1 module at 730 of FIG. 33.

Figure 36:
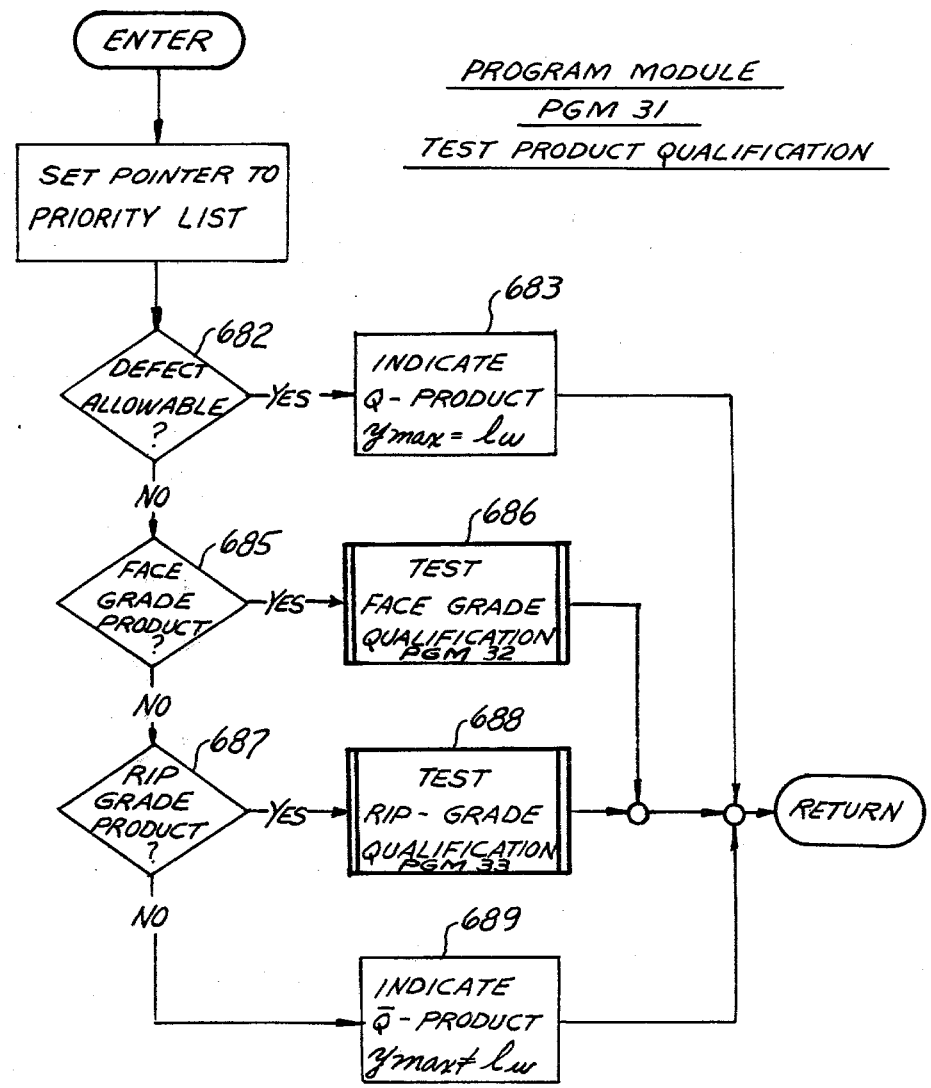
FIG. 36 is a flow diagram for program module PGM31.

The details of the defect analysis performed in the Test Product Qualification block 677 of program module PGM3 are shown on FIG. 36. Each defect within the template is sequentially analyzed from left to right and compared with the allowable defects contained in the order entry list stored in the product order buffer.

Program Module PGM31 is entered and the pointer initialized as indicated. Each defect within the area defined by the template is analyzed as indicated by block 682 to determine if the defects are allowable. If the defects are allowable, the product is designated as a qualified product as indicated by block 683, $y_{max}$ remains equated to the exit coordinate of the template and process control returns to PGM3 at block 679 and the product is designated as a qualified (Q) product. If a non-allowable defect is encountered within the template area, the product is further analyzed to determine whether it is a Face-grade product as indicated by block 685 or a Rip-grade product as indicated by block 687. If the product is neither a face or rip grade product, it is designated as an unqualified ($\overline{Q}$) product as indicated by block 689, $y_{max}$ is equated to the right-most flaw boundary and process control returns to block 679 of FIG. 35.

It should be realized that the relevancy of extracting rip-grade or face-grade products as opposed to merely satisfying a simple product list requiring only cross-cut saw cuts depends upon the board product requirements of the facility for which the inspection and optimization are being performed. The following test for determining face-grade quality products is performed in program module PGM32 shown on FIG. 37. Program Module PGM32 then accesses program module PGM34 shown on FIG. 38. The test for rip-grade lumber qualification is performed by Program Module PGM33, shown in FIG. 39.

The purpose of program module PGM32 is to test the extent of flaw penetration for face-grade products. To qualify as a face-grade product, non-allowable defects cannot occur on both faces, i.e., a single flaw which simultaneously penetrates or two non-penetrating flaws which lie on alternating faces are not allowed for the product to qualify as a face-grade product. In essence, the face-grade product must have a virtually clear side containing only acceptable flaws.

Figure 37:
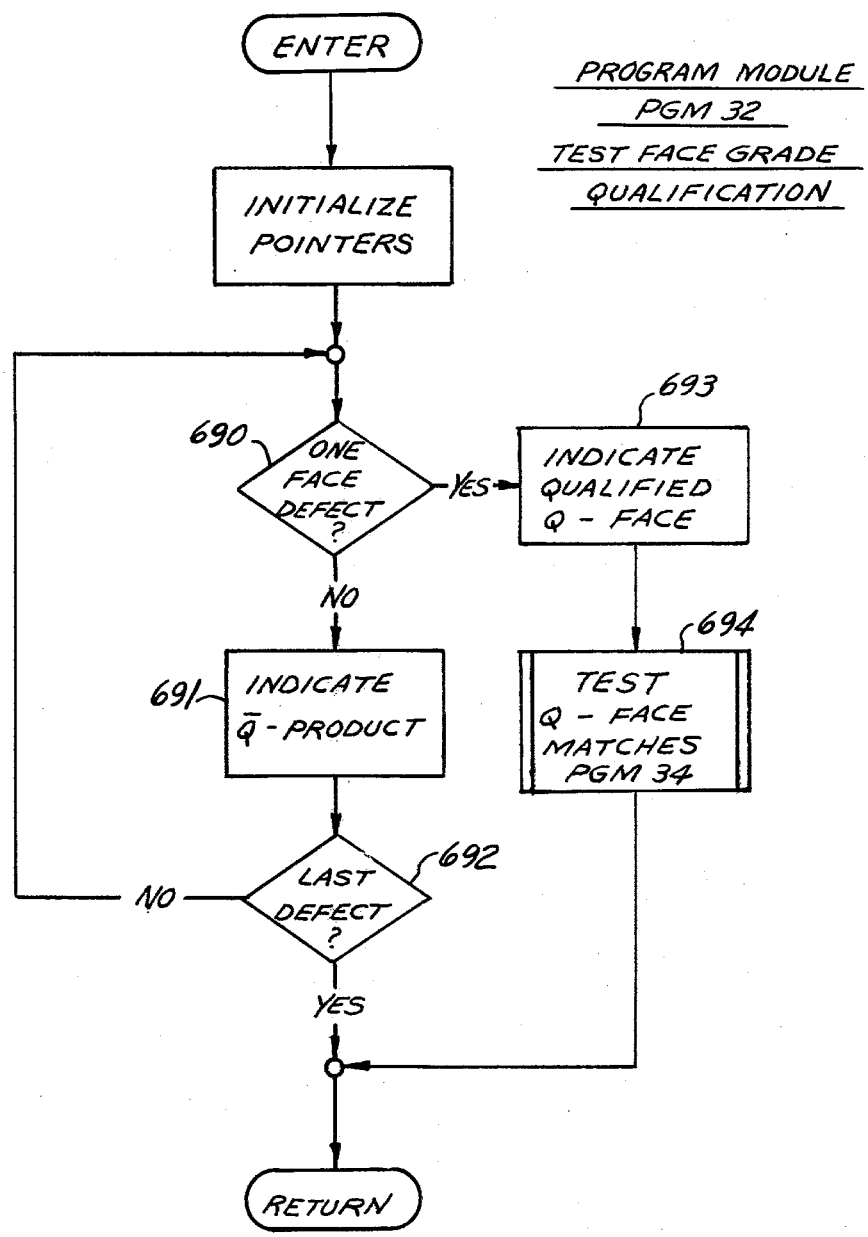
FIG. 37 is a flow diagram for program module PGM32.

Referring to FIG. 37, the detailed flow of module PGM32 is shown. Each defect within the area of the template is examined to determine the flaw class and face index F of each flaw. The analysis proceeds to determine if each non-allowable defect is one or two sided as indicated by block 690. Defect analysis proceeds from left to right within the confines of a template. The program loops through all the remaining defects within the template. If a particular defect is non-penetrating, i.e., one faced, the defect is identified as potentially qualifying as a face-grade product (Q) as indicated 693; the face code for each non-penetrating defect is stored for later use in module PGM34. Subsequently, the one sided flaws found within the template area are examined in the Test Q Face Matches indicated by block 694 and performed by program module PGM34, the existence of non-allowable defects on alternating faces are determined.

Figure 38:
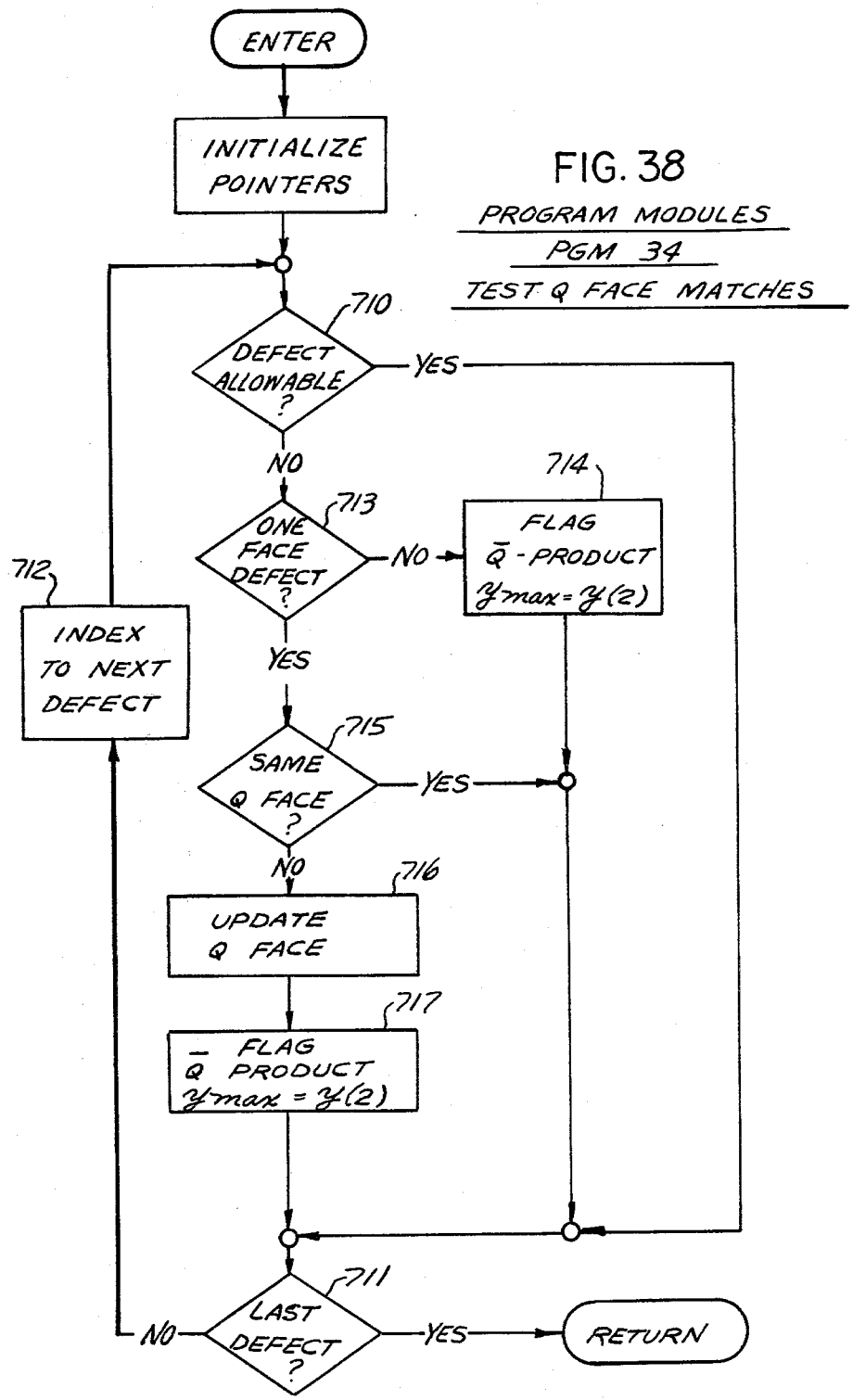
FIG. 38 is a flow diagram for program module PGM34.

A detailed flow diagram of the Test Q Face Matches, program module PGM34, is shown in FIG. 38. Defect quality of the defects stored by Program Module PGM32 are again analyzed as indicated by block 710, by comparing the defect index $D_j$ to the lists of allowable defects contained on the product list. If the defect is allowable and is not the last within a template boundary, the process is indexed to the next defect as indicated by block 712, and the analysis repeats. If the defect being tested is the last defect within the boundaries of the template, process control is returned to program module PGM32 as indicated by block 711. If the defect is a non-allowable flaw, it is further tested in block 713 to see if it is a non-penetrating or one face defect. If it is not a one-faced defect, the acceptance pointer is shifted to the exit dimension $y_2(i)$ of the non-qualifying flaw 714 to generate an exclusion of defect line at $y_2(i)$ for the $i^{th}$ defect. The effect of the manipulations performed in block 714 is to identify a non-qualifying product having dimension $y_1-y_2(i)$. If the defect is one-sided, a decision is made to determine if the non-allowable defect resides on the same side for face of the piece as those previously processed flaws as indicated by block 715. If the non-allowable defect resides upon the same side as any previously analyzed defect, the analysis proceeds to the next defect, continuing from left to right within the template. If it is determined in block 715 that a non-allowable defect resides on a face opposite to those non-allowable flaws previously considered, the defect pointer is moved to the exit dimension of the particular flaw to generate an exclusion of defect line at $y_2(i)$ in the block 716. The board within the template boundary is designated as a non-qualifying ($\overline{Q}$) face-grade product as indicated by block 717. If a face grade piece cannot be extracted, the process flow returns to PGM31.

Figure 39:
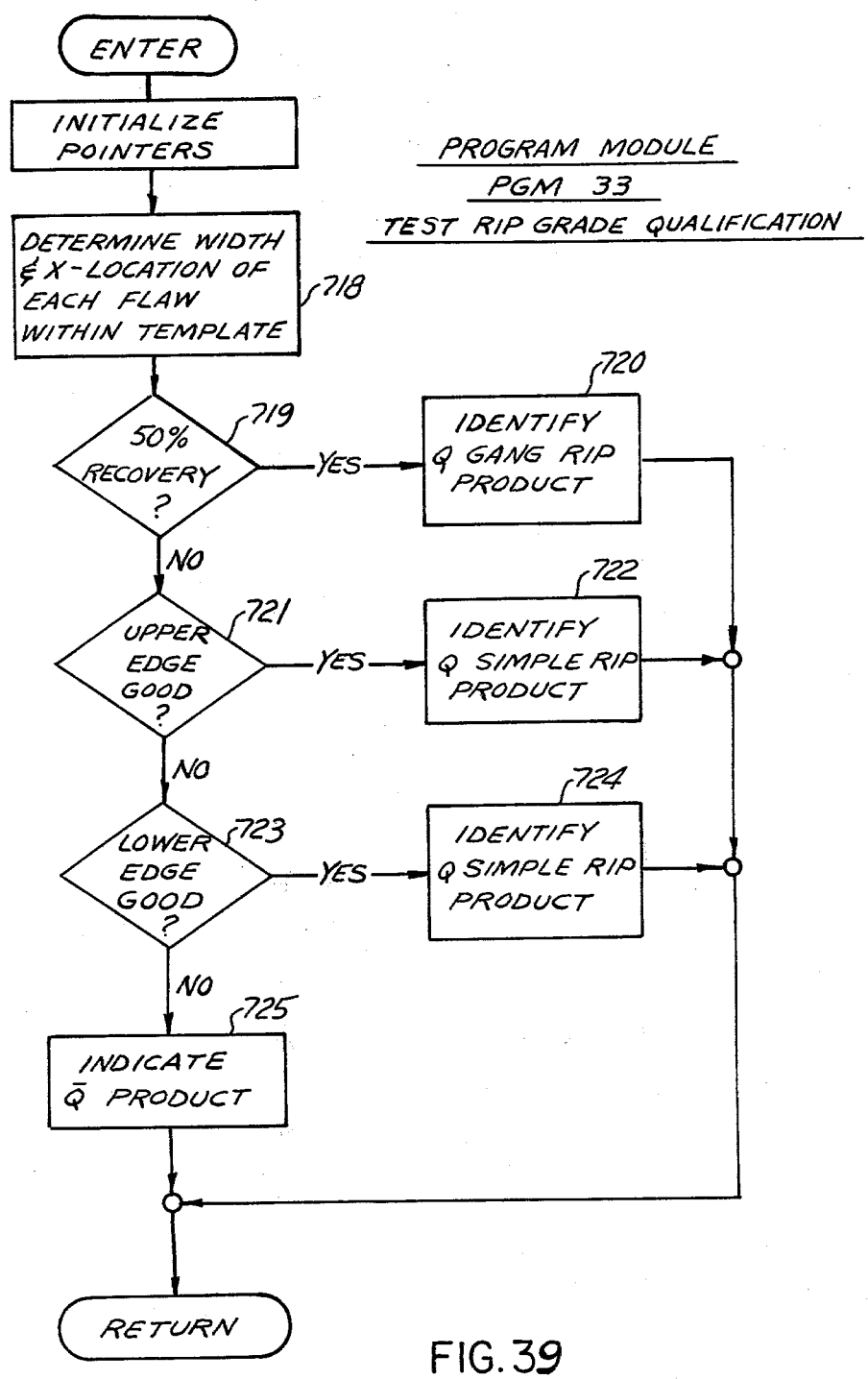
FIG. 39 is a flow diagram for rip grade qualification test.
Figure 40:
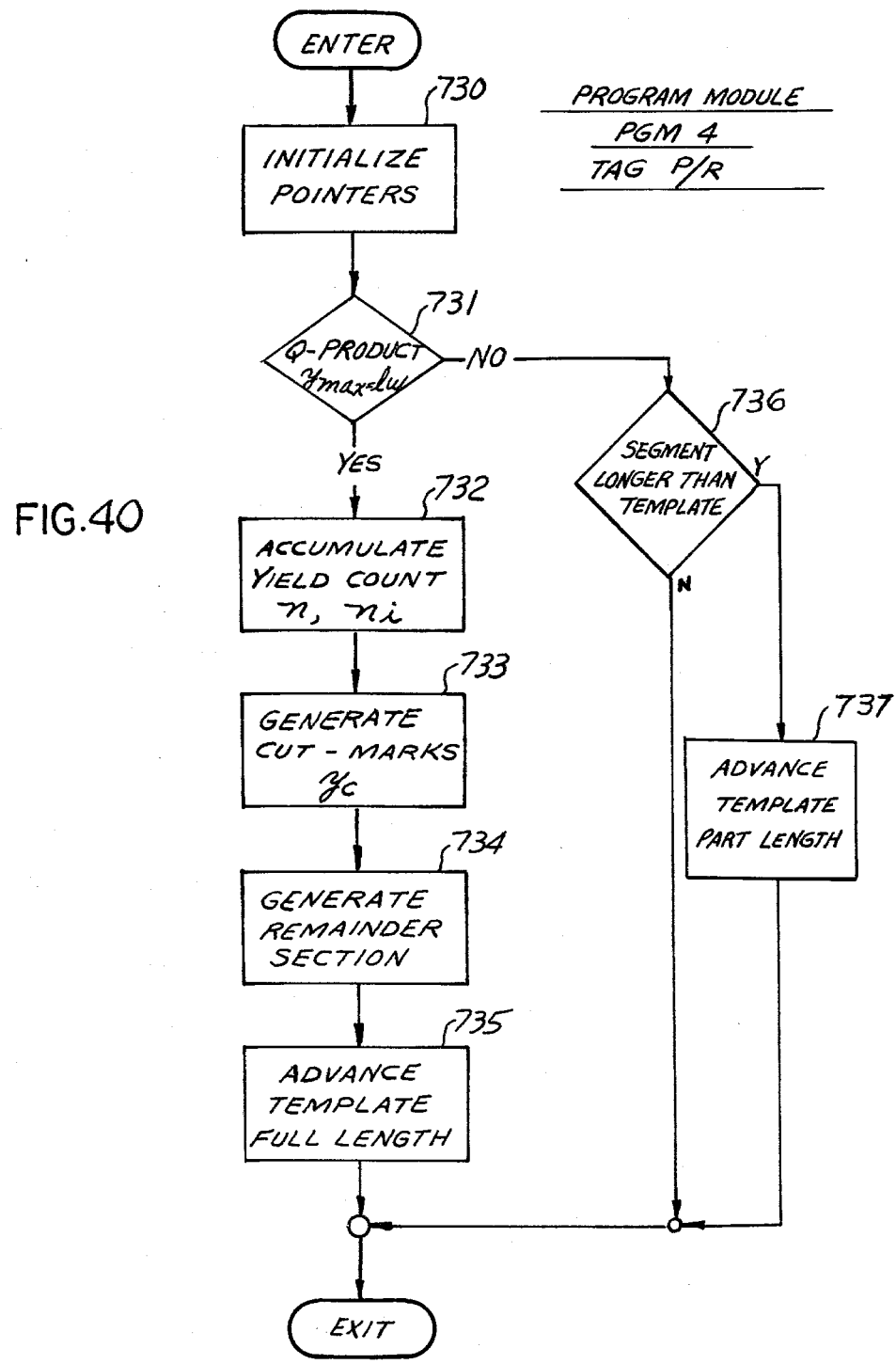
FIG. 40 is a flow diagram for program module PGM4.

The flow diagram of Program Module PGM33, block 688 of FIG. 36 is illustrated in FIG. 39. The width location of each flaw within the boundaries of the template are first determined as indicated by block 718. The potential product is then analyzed to determine if at least 50% of the width of the wood is recoverable as indicated by block 719. If every flaw in the template is such that a single piece having a width of 50% or greater can be recovered, the product is designated as a qualified rip product as indicated by block 720.

If the 50% criteria cannot be satisfied, the Program Module next examines the extent of the upper and lower edges of the wood within the template to determine if all non-allowable defects can be excluded by rip cutting the non-allowable flaws from either edge of the wood as indicated by blocks 721 and 723 respectively. If a gang or single rip-grade product cannot be extracted based upon the originally selected template, the product is designated as a $\overline{Q}$ product as indicated by block 725 and process control is then returned to program module PGM3, with the acceptance pointer marking the non-allowable location. If all of the non-allowable defects can be excluded by rip cutting, the non-allowable flaws from either edge, the product is identified as a qualified Q simple rip product as indicated by block 722 or 724.

Having analyzed the defects within the selected template, it is necessary to generate cross-cut sawing locations ($y_c$) for the qualified products. This process is performed in Program Module PGM4 entitled as TAG P/R identified as block 730 on FIG. 33. A detailed flow diagram of Program Module PGM4 is shown in FIG.

40. A product is designated as qualifying for cutting if the acceptance indication $y_{max}$ points to the trailing edge or right-most edge of the product template in board coordinates. Cut-marks $y_c$ are generated at $y_1(c) = y_{max}$ and at $y_2(c) = y_{max} -$ template length. Any remainder piece is identified. This remainder will ultimately be processed as pieces of good wood that may later yield products designated within the product list. For any identified remainder, the Remainder number r, the beginning location $y_1(r)$ and exit location $y_2(r)$ and the board number k, are stored in the remainder buffer using the format of FIG. 27. An example of a typical remainder generated after the selection of a qualified product from a segment is pictorially shown in FIG. 24.

The acceptance pointer value is tested in block 731 to determine if a qualified product can be extracted. If there exists a qualified product, then inventory yield data is accumulated designating the total number of pieces n cut against the order list as well as the total number of pieces $n_p$ cut to the $p^{th}$ product, as indicated by block 732. This data is stored in the yield buffer using the format of FIG. 27.

Two cut-marks are then generated as indicated 733, the first $y_1(c)$ at the entry location the template $y_1(s)$ and the second $y_2(c)$ at exit location $1_w$ of the template. The $y_2(c)$ and the exit location of the segment $y_2(s)$ are equated with the beginning $y_1(r)$ and exit $y_2(r)$ location of a remainder piece and are stored in the remainder buffer as indicated by block 734. The product template is numerically advanced as indicated by block 735 so that the left edge of the template is coincident with the right side or second cut-mark of the qualified product and Program Module PGM4 is exited and the process returns to block 470 of Program Module EXEC1 shown on FIG. 33. If no qualified product is identified by the analysis of block 731, the process next tests to determine if the segment is longer than the template as shown by block 736. If it is not, the Program Module PGM4 is exited and the process returns to block 470 of Program Module EXEC1. If the segment is longer than the template, the template is shifted to the right as shown in block 737 so that its left hand boundary is coincident with the right edge of the last non-acceptable defect found within the boundary of the template in its original position and PGM4 is exited. The EXEC1 program determines whether or not the same template can be fit within the remainder of the segment being processed. If it can, then the quality of the flaws within this section of wood is processed as indicated by block 670 of FIG. 33 as though the remainder was a piece of wood initially designated as a segment. If the original template does not fit the remainder, the template for the next priority product is obtained and the process is repeated with the next template.

The cut-mark data stored in the cut-mark buffer can be considered as an unsorted tabulation of the multiplicity of potential saw cuts. It is necessary to restructure the data within the cut-mark buffer to facilitate the physical sawing or marking of each product. The Program Module PGM5 controls the editing and sorting of these cut-mark locations. The output of this module consists of single valued sawing locations $y_c(c)$ in ascending order, i.e., increasing board coordinate units.

Methods of restructuring data are well known in the art, however, a brief discussion of the method used is presented on FIG. 41. Referring to FIG. 41, Program Module PGM5 is entered and indices initialized. The program reviews the unsorted cut-mark data within the cut-mark buffer identifying the cut-mark closest to the left edge of the $k^{th}$ board, that is the cut-mark having the lowest coordinate value excluding the left edge of board as indicated by block 800. During this initial scanning of the cut-mark buffer data, duplicate valued cut-marks are eliminated.

After ascertaining the lowest value cut-mark, each cutmark is subsequently reexamined saving only the value of the particular cut mark having the next highest coordinate value. This process is continued until a reordered cutmark list is obtained as indicated by block 802. Upon completion of the cutmark reordering process for the $k^{th}$ board, processing for that board is finished.

With the completion of the processing, the locations where the board is to be marked or cut is available to the output device 22. When the board is received in the output device, the output device interrogates the buffer storing the cutline data and either marks or cuts the board at the determined locations.

Having described the lumber inspection and optimization system, and in particular the process for determining the cut line locations which produce an optimum utilization of the material,

What is claimed is:

1. In combination with an electro-optical scanner generating encoded scan data indicative of the size, shape, and locations of random flaws detected on the surfaces of a piece of raw material, a system for optimizing product selection and utilization of the raw material comprising:
   flaw data processor means for processing said encoded scan data to generate a flaw data buffer storing edge location data indicative of the location of the edges of a rectangle formed about each flaw;
   product order entry means for generating in response to inputs from an external source an order entry buffer storing order entry data indicative of the products desired to be taken from the raw material, said order entry data including a physical description and an assigned priority for each product stored in said order entry buffer;
   segment buffer generator means for analyzing said edge location data stored in said flaw data buffer to generate a segment buffer storing the end location of usable segments of material between the random flaws;
   product selection means for selecting said products from the usable segments of material stored in said segment buffer, said means selecting said products in the order of their priority; and
   means for generating cut line data indicative of the beginning and end locations of each selected product.

2. The combination of claim 1 wherein the electro-optical scanner generates sequential frames of encoded scan data, each frame indicative of a predetermined scan area and said sequential frames indicative of adjacent scan areas, said flaw data processor means includes means for processing said frames of scan data one at a time in the order in which they are generated.

3. The combination of claim 1 wherein said flaw data processor means further includes means for enlarging the rectangles formed about each flaw said enlarged rectangles encompassing defective material normally adjacent to the flaws and wherein said flaw data buffer stores the edge locations of said enlarged rectangles.

4. The combination of claim 3 wherein said scanner means generates encoded scan data coded to distinguish scan data indicative of long narrow flaws from all other flaws, said means for generating edge location data indicative of enlarged rectangles about each flaw further includes means responsive to the scan data code for generating edge location data indicative of an enlarged rectangle about long narrow flaws according to a first predetermined set of rules and for generating edge location data indicative of enlarged rectangles about said all other flaws according to a second predetermined set of rules.

5. The combination of claim 4 wherein said means for generating edge location data indicative of enlarged rectangles about each flaw further includes means responsive to the length and width of each of said all other flaws for generating said edge location data indicative of enlarged rectangles about each flaw having a length to width ratio greater than one according to a third predetermined set of rules and for generating said edge location data indicative of enlarged rectangles about each flaw having a length to width ratio less than one according to a fourth predetermined set of rules, and wherein said second set of rules comprises said third and fourth set of rules.

6. The combination of claims 1 or 5, wherein said product selection means comprises:
   first means for selecting products from said usable segments in the order of the priority of said products;
   means for generating a remainder buffer storing remainder data indicative of the beginning and end locations of usable remainder material after the selection of said product by said first means;
   second means for selecting products from said usable remainder material in the order of the priority of said products.

7. The combination of claim 6 wherein said means for generating cut line data generates cut line data indicative of the beginning and end locations of the products selected from said segments and said usable remainder material.

8. The combination of claim 1 wherein said order entry data includes products having allowable classes of flaws, said system further includes an inspection station having a flaw class data generator means for generating flaw class data in response to inputs from a human inspector indicative of the location and class of each flaw, said flaw classes including allowable flaws and totally non-allowable flaws;
   said flaw data processor means further includes means for combining said flaw class data with the associated edge location data to generate combined flaw data and storing said combined flaw data in said flaw data buffer;
   said segment buffer generator means generates a segment buffer storing the edge locations of usable segments between only the totally non-allowable random flaw; and
   said product selection means selects said products including the products having allowable flaws from said usable lengths of material in accordance with a descending order of priority.

9. The combination of claim 8 wherein said flaw data processor means further includes means for enlarging the rectangles formed about each flaw encompassing defective material normally adjacent to the flaws and wherein said flaw data buffer stores said edge location data.

10. The combination of claim 8 wherein said scanner means generates encoded scan data coded to distinguish scan data indicative of long narrow flaws from all other flaws, said means for generating edge location data indicative of enlarged rectangles about each flaw further includes means responsive to the scan data code for generating edge location data indicative of enlarged rectangles about long narrow flaws according to a first predetermined set of rules and for generating edge location data indicative of enlarged rectangles about said all other flaws according to a second predetermined set of rules.

11. The combination of claim 10 wherein said means for generating edge location data indicative of enlarged rectangles about each flaw further includes means responsive to the length and width of each of said all other flaws for generating said edge location data about each flaw having length to width ratio greater than one according to a third predetermined set of rules and for generating said edge locacation data about each flaw having a length to width ratio less than one according to a fourth predetermined set of rules, and wherein said second set of rules comprises said third and fourth set of rules.

12. The combination of claim 8 wherein product selection means comprises:
   first means for selecting said products from said usable segments stored in said segment buffer in the order of their priority;
   means for generating a remainder buffer storing remainder data indicative of the beginning and end locations of usable remainder material after the selection of said products by said first means; and
   second means for selecting said products from said usable remainder material in the order of their priority.

13. The combination of claim 12 wherein said means for generating a cut line data generates cut line data indicative of the beginning and end locations of the products selected from said usable segment and usable remainder materials.

14. The combination of claim 12 wherein said first and second means for selecting comprises:
   means for extracting from said order entry buffer the data indicative of the physical description of the products in their order of priority, said physical description including the length of the product and the classes of allowable flaws;
   means for comparing the length of each extracted product against the beginning and end location data stored in said segment and remainder buffers respectively, to identify the highest priority products that may be taken;
   means for testing the class of each flaw along the length of the usable segment and remainder material encompassed by the length of the identified product against the allowable flaw classes for the identified product to designate said identified product as a selected product when all the flaws are allowable; and
   means responsive to the designation of the identified product as a selected product for generating product location data indicative of the beginning and end location of said selected product.

15. The combination of claim 12 wherein said order entry data further includes face-grade products having non-allowable flaws permitted on only one face of said product, said means for comparing the class of each flaw further includes means determining on which face the non-allowable flaws occur and designating said identified product as a selected face grade product when all the non-allowable flaws occur on the same face.

16. The combination of claim 11 or 12 wherein said order entry data includes rip grade products in which the width of the rip grade product is less than the width of the material, said means for comparing the class of each flaw further includes means responsive to the order entry data indicative of the identified product being a rip grade product and the location of the non-allowable flaws for designating said identified product as a selected rip grade product when the width of the usable segment material exceeds predetermined minimum width.

17. The combination of claim 16 wherein said means for comparing the class of each flaw further includes means responsive to the order entry data indicative of the identified product being a rip grade product for designating said identified product as a selected rip grade product when either edge of the material is free of non-allowable flaws.

18. A method for optimizing the product utilization of raw material having flaws of irregular shapes and sizes randomly disposed along its surfaces wherein the surfaces of the material are electro-optically scanned to generate encoded scan data, indicative of the size, shape, and location of the flaws including the surface of the material on which they occur, said method comprising the steps of:
processing said encoded scan data to generate edge location data indicative of the location of the edges of rectangles formed about each flaw;
storing said edge location data in a flaw data buffer;
generating order entry data in response to an input from an external source indicative of the physical description and priority of the products desired to be obtained from the raw material;
storing said order entry data in an order entry buffer, in a descending order of the priority;
selecting products to be cut from said raw material in accordance with said stored descending order of the priority from the usable material between the flaws determined from the edge location data stored in said flaw data buffer; and
storing the beginning and the end locations of each selected product to generate a cut line buffer storing the locations where the material is to be cut to optimize the utilization.

19. The method of claim 18 wherein said surfaces are electro-optically scanned to generate frames of encoded scan data, each of said frames indicative of predetermined sequential scan area along the surface of said raw material, said step of processing the encoded scan data, sequentially processes each frame of encoded scan data one frame at a time in the order in which said frames are generated.

20. The method of claim 19 wherein said step of processing said frames of encoded scan data to generate edge location data further includes the steps of:
enlarging the rectangles formed about each flaw to generate new edge location data encompassing defective material normally adjacent to the flaws; and
storing the new edge location data indicative of the enlarged rectangles in said flaw data buffer.

21. The method of claim 20 wherein the scanner generates encoded scan data coded to distinguish scan data indicative of long narrow flaws from all other flaws said step for enlarging the rectangles generated about each flaw further includes the steps of:
generating new edge location data in response to coded scan data indicative of long narrow flaws according to a first predetermined set of rules; and
generating new edge location data in response to said coded scan data indicative of said all other flaws according to a second predetermined set of rules.

22. The method of claim 21 wherein said step of generating new edge location data in response to coded scan data indicative of said all other flaws further includes the steps of:
computing from said scan data the length to width ratio of each of said all other flaws;
generating new edge location data for each of said all other flaws having a length to width ratio greater than one according to a third predetermined set of rules; and
generating new edge location data for each flaw having a length to width ratio less than one according to a fourth predetermined set of rules; and
wherein said second set of rules comprises said third and fourth set of rules.

23. The method of claim 18 or 21 wherein said step of selecting products comprises the steps of:
generating segment data from said edge location data indicative of the beginning and the end locations of usable segment materials between said flaws;
storing said segment data in a segment buffer;
selecting from said usable segment material said products stored in said order entry buffer in the order of the priority in which said products are stored;
generating remainder data indicative of the beginning and end locations of the usable remainder material after the selection of said products;
storing said remainder data in a remainder buffer;
selecting from said usable remainder material said products stored in said order entry buffer in the order of priority in which said products are stored.

24. The method of claim 21 wherein said step of storing to generate a cut line buffer stores the beginning and end locations of the products selected from said segment and said usable remainder material.

25. The method of claim 19 wherein said order entry data includes products having allowable classes of flaws said method further includes the steps of:
generating flaw class data in response to inputs from a human inspector indicative of the class of each flaw detected during the electro-optical scanning said flaw class data including said allowable flaws and non-allowable flaws; and
wherein said step of processing said scan data further includes the steps of combining the edge location data indicative of the rectangles about each flaw with the flaw class data associated with each flaw to generate combined flaw data; and
storing said combined flaw data in said flaw data buffer; and
said step of selecting said products selects said products in accordance with a descending order of priority and the edge location data corresponding to rectangles formed about the non-allowable flaws.

26. The method of claim 25 wherein said step of processing said frames of encoded scan data to generate edge location data further includes the steps of:

enlarging the rectangles formed about each flaw encompassing the defective material normally adjacent to the flaws to generate new edge location data; and storing said new edge location data indicative of the enlarged rectangles in said flaw data buffer.

27. The method of claim 26 wherein the scanner generates encoded scan data coded to distinguish scan data indicative of long narrow flaws from all other flaws said step of enlarging the rectangles generated about each flaw further includes the steps of:

enlarging in response to coded scan data indicative of long narrow flaws the rectangle formed about said long narrow flaws according to a first predetermined set of rules; and enlarging in response to said encoded scan data the rectangles formed about all other flaws according to a second predetermined set of rules.

28. The method of claim 27 wherein said step of enlarging in response to said encoded scan data the rectangles formed about all other flaws further includes the steps of:

computing from said flaw data the length to width ratio for each of said all other flaws;

enlarging the rectangles formed about each of said all other flaws having a length to width ratio greater than one according to a third predetermined set of rules; and enlarging the rectangles formed about each of said all other flaws having a length to width ratio less than one according to a fourth predetermined set of rules; and wherein said second set of rules comprises said third and fourth set of rules.

29. The method of claim 23 wherein said step of selecting products comprises the steps of:

generating segment data from said edge location data indicative of the beginning and end locations of usable segment material between said non-allowable flaws;

storing said segment data in a segment buffer;

selecting the highest priority products that may be taken from the usable segment material defined by the segment data;

subtracting the length of the selected product from the segment data to generate remainder data indicative of the beginning and the end locations of usable remainder material after the removal of said selected product from said segments;

selecting the highest priority product that may be taken from said usable remainder material defined by said remainder data; and wherein said step of storing to generate a cut line buffer stores cut line data indictive of the beginning and the end locations of the products selected from said segments and usable remainder material.

30. The method of claim 29 wherein said step of selecting from the usable segment material comprises the steps of:

extracting from said order entry buffer the data indicative of the physical description of the products in the order of their priority said physical description including length of the product and classes of allowable flaws;

comparing the length of each extracted product against the beginning and the end location data stored in the segment buffer to identify the highest priority product that may be taken from the usable segment material;

comparing the class of each flaw along the length of the usable segment material encompassed by the length of the identified product with the allowable flaw classes of the identified product to designate a selected product when all of the encompassed flaws are of allowable classes.

31. The method of claim 29 wherein said step of selecting from the usable remainder material comprises the steps of:

extracting from said order entry buffer the data indicative of the physical description of the products in the order of their priority said physical description including length of the product and classes of allowable flaws;

comparing the length of each extracted product against the beginning and the end location data stored in the remainder buffer to identify the highest priority product that may be taken from the usable material;

comparing the class of each flaw along the length of the usable remainder material encompassed by the length of the identified product with the allowable flaw classes of the identified product to designate a selected product when all of the encompassed flaws are of allowable classes.

32. The method of claim 31 wherein said order entry data further includes face grade products permitting non-allowable flaws on only one face of said product said step of selecting products from said usable segment and remainder material further includes the step of:

determining from said flaw data the face of the material on which each of said non-allowable flaws occurs;

generating a signal identifying the identified product as a selected product of face grade quality when all of the non-allowable flaws encompassed by the identified product are disposed on only one face of the material.

33. The method of claim 32 wherein said order entry data further includes rip grade products in which the width of the rip grade product is less than the width of the material, said step of testing the class of each flaw further includes the step of:

computing from the flaw data the width of the usable segment and remainder material;

comparing the width of the usable segment and remainder material to a predetermined minimum width; and identifying the product as a selected product of rip grade quality when the width of the usable segment and remainder material is greater than the predetermined width.

34. A method for optimizing the board product utilization of raw lumber having flaws of irregular shapes and sizes randomly disposed along its surfaces wherein the surfaces of the lumber are electro-optically scanned to generate encoded scan data indicative of the size, shape, and location of the flaws including the surface on which the flaws occur, said method comprising the steps of:

processing said encoded scan data to generate edge location data indicative of the edge locations of a rectangle formed about each flaw;

computing from said edge location data in accordance with a predetermined set of rules new edge location data indicative of rectangles about each flaw enlarged to encompass defective wood normally adjacent to each flaw;

storing said new edge location data to generate a flaw data buffer;

generating order entry data in response to an input from an external source indicative of the physical description and priority of the board products desired to be obtained from the raw lumber;

storing said order entry data to generate an order entry buffer storing the physical description of each board product in the order of its priority;

processing said flaw data to generate segment data indicative of the beginning and end locations of usable segments of lumber between the detected flaws;

storing said segment data to generate a segment buffer;

comparing in the order of their priority, the length of the board products stored in the order entry buffer with the lengths of the usable segments of lumber stored in the segment buffer to identify the highest priority board product that may be taken from each usable segment;

computing the beginning and end locations of the identified highest priority board products taken from usable segments to generate cut line data indicative of the locations where the raw lumber is to be cut to obtain the identified board product;

subtracting said cut line data from said segment data to generate remainder data indicative of the beginning and end locations of usable remainder lumber;

storing said remainder data to generate a remainder buffer;

comparing in the order of priority, the lengths of the board products stored in the order entry buffer with the length of usable remainder stored in the remainder buffer to identify the highest priority board product that may be taken from each usable remainder;

computing the beginning and end location of the identified highest priority board products taken from usable remainder to generate cut line data indicative of the locations where the raw lumber is to be cut to obtain the identified board product;

subtracting said cut line data from said remainder data to generate new remainder data indicative of the beginning and end locations of remaining remainder lumber;

repeating the steps of comparing to identify highest priority board products, computing to generate cut line data, and subtracting to generate new remainder data until no board products stored in the order entry buffer can be extracted from the usable remainder material; and storing said cut line data to generate a cut line buffer.

35. The method of claim 34 wherein said order entry data includes board products having allowable classes of flaws, said method further comprises the steps of:

generating flaw class data in response to inputs from an external source indicative of the class of each flaw detected during the electro-optical scanning, said flaw class data including allowable and nonallowable flaws;

wherein said step of storing to generate a flaw data buffer further stores said flaw class data with the associated edge location data and said flaw data for each flaw is indicative of the flaw location and flaw class;

said step of processing said flaw data to generate segment data generates segment data indicative of the beginning and end locations of usable segments of lumber between the nonallowable flaws; and said method further includes after each step of comparing to identify the highest priority board product that may be taken from usable segment and usable remainder, the step of comparing the class of each flaw along the length of each usable segment and usable remainder encompassed by the identified board product to the allowable flaw classes of the identified board product to reject all identified board products having nonallowable flaws, and repeat the step of comparing starting with the next lowest priority board product.

36. The method of claim 35 wherein said order entry data further includes face grade board products permitting non-allowable flaws on only one face of said product said method further includes after the step of comparing the class of each flaw the steps of:

determining from said flaw data the face of the lumber on which said non-allowable flaws occur; and generating a signal identifying the identified board product as a board product of face grade quality when all of the non-allowable flaws encompassed by the identified product are disposed on only one face.

37. The method of claim 35 or 36 wherein said order entry data further includes rip grade board products in which the width of the rip grade products is less than the width of the raw lumber, said method further includes the steps of:

computing from the flaw data the width of the usable segment and remainder lumber;

comparing the width of the usable segment and remainder lumber to predetermined minimum width; and identifying the board product as rip grade quality when the width of the usable segment and remainder lumber is greater than the predetermined minimum width.

* * * * *